US012616823B2

(12) United States Patent
Gill et al.

(10) Patent No.: US 12,616,823 B2
(45) Date of Patent: May 5, 2026

(54) SUSTAINED RELEASE FORMULATIONS IN DELIVERY DEVICES

(71) Applicant: ARGENTA INNOVATION LIMITED, Auckland (NZ)

(72) Inventors: David Anthony Gill, Auckland (NZ); Desmond Ian John Morrow, Auckland (NZ); Michael Venning, Auckland (NZ)

(73) Assignee: ARGENTA INNOVATION LIMITED, Auckland (NZ)

( * ) Notice: Subject to any disclaimer, the term of this patent is extended or adjusted under 35 U.S.C. 154(b) by 758 days.

(21) Appl. No.: 17/274,599

(22) PCT Filed: Sep. 10, 2019

(86) PCT No.: PCT/NZ2019/050119
§ 371 (c)(1),
(2) Date: Mar. 9, 2021

(87) PCT Pub. No.: WO2020/055270
PCT Pub. Date: Mar. 19, 2020

(65) Prior Publication Data
US 2022/0047855 A1 Feb. 17, 2022

(30) Foreign Application Priority Data

Sep. 10, 2018 (NZ) ........................................ 746209

(51) Int. Cl.
*A61M 31/00* (2006.01)
*A61D 7/00* (2006.01)
(Continued)

(52) U.S. Cl.
CPC ............. *A61M 31/002* (2013.01); *A61D 7/00* (2013.01); *A61K 9/0068* (2013.01); *A61K 45/06* (2013.01);
(Continued)

(58) Field of Classification Search
CPC ........ A61M 31/002; A61M 2205/3334; A61M 2250/00; A61M 2205/0255;
(Continued)

(56) References Cited

U.S. PATENT DOCUMENTS 3,056,724 A * 10/1962 Marston ................. A23K 40/35
424/490
4,671,789 A * 6/1987 Laby ........................ A61D 7/00
604/93.01
(Continued)

FOREIGN PATENT DOCUMENTS

AU 227098 3/1960
AU 2005209631 3/2006
(Continued)

OTHER PUBLICATIONS

Szüts, Study of gel-forming properties of sucrose esters for thermosensitive drug delivery systems, 2010, International Journal of Pharmaceutics (Year: 2010).*
(Continued)

*Primary Examiner* — Rebecca E Eisenberg
*Assistant Examiner* — Brandon W. Levy
(74) *Attorney, Agent, or Firm* — Dentons Bingham Greenebaum LLP; Brian W. Chellgren

(57) ABSTRACT

An intra-ruminal device includes a body substantially impervious to rumen fluid, the body including a barrel, at least one outlet, at least one matrix including at least one active ingredient and at least one clay mineral, a compression arrangement and at least one variable geometry device dependent from the body. Use of the intra-ruminal device and a method of treating a ruminant animal by administering the intra-ruminal device to the animal are also disclosed.

20 Claims, 8 Drawing Sheets

(51) Int. Cl.
  *A61K 9/00* (2006.01)
  *A61K 45/06* (2006.01)
  *A61K 47/02* (2006.01)

(52) U.S. Cl.
  CPC ..... *A61K 47/02* (2013.01); *A61M 2205/3334* (2013.01); *A61M 2250/00* (2013.01)

(58) Field of Classification Search
  CPC ...... A61M 2207/00; A61M 2210/1053; A61M 25/04; A61D 7/00; A61K 9/0068; A61K 45/06; A61K 47/02; A61K 9/0002; A61K 9/0092; A61K 9/2009; A61K 31/00; A61K 31/4188; A61K 9/48; A61K 9/4808; A61K 9/4816; A61K 9/0065; A61K 9/5015; Y02P 60/22; A23K 40/35; A23K 50/10; A61J 3/07
  See application file for complete search history.

(56) References Cited

U.S. PATENT DOCUMENTS

| | | | |
|---|---|---|---|
| 4,687,480 A | | 8/1987 | Laby et al. |
| 5,277,912 A | | 1/1994 | Lowe et al. |
| 5,951,538 A | * | 9/1999 | Joshi ................... A61M 31/002 |
| | | | 604/502 |
| 9,717,693 B2 | | 8/2017 | Bettini et al. |
| 9,956,292 B2 | * | 5/2018 | Pimentel ................. A61P 43/00 |
| 2005/0064032 A1 | | 3/2005 | Lowe |
| 2008/0317820 A1 | * | 12/2008 | Rathbone ........... A61M 31/002 |
| | | | 424/438 |
| 2018/0310592 A1 | * | 11/2018 | Embree .................. A23K 50/10 |

FOREIGN PATENT DOCUMENTS

| | | |
|---|---|---|
| NZ | 554633 | 11/2008 |
| WO | WO 1982000094 | 1/1982 |
| WO | WO 2011014078 | 2/2011 |
| WO | WO 2019164410 | 8/2019 |

OTHER PUBLICATIONS

Cardinal, Intraruminal devices, 1997, Advanced Drug Deliver Reviews, 28, 303-322 (Year: 1997).*

Extended Search Report, EP Patent Application No. 19860212.0, dated May 11, 2022.

International Search Report and Written Opinion, mailed Mar. 19, 2020—International application No. PCT/NZ2019/050119; Applicant: Argenta Innovation Limited.

* cited by examiner

Figure 7

SUSTAINED RELEASE FORMULATIONS IN DELIVERY DEVICES

FIELD OF THE INVENTION

The present invention relates to an intra-ruminal device comprising a formulation that allows for sustained, controlled delivery of one or more active therapeutic ingredients to a ruminant animal.

BACKGROUND TO THE INVENTION

The delivery of pharmaceutically active ingredients or other substances to an animal in a sustained and controlled manner is desirable. Various devices and methods to deliver active ingredients to ruminants are known in the art. However, a number of these continue to be limited by their.

inability to effectively control the delivery rate of a therapeutic agent over an extended period of time, and/or.

limited payout duration, and/or ability to maintain a reproducible dose-rate due to, for example, variability in delivery rate and/or product failure.

Such problems may lead to potential toxicity from over-dosing or poor efficacy from under-dosing. Sub-therapeutic levels of certain therapeutics such as anti-parasitic or anti-microbial products may lead to other problems, for example, the development of drug resistant micro-organisms.

Existing sustained release technologies for the oral delivery of therapeutics to ruminants have limited duration of up to approximately 150 days. Extending the release period from a device may be beneficial for the delivery of selected actives where a single application could replace multiple applications, thereby reducing the number of associated dosage breaks, and/or.

the potential for peaks and troughs in the therapeutic period, and/or reducing the cost of treatment.

Providing substantial increases in the sustained release period without compromising linearity of dose in a device that maintains an acceptable size for oral delivery may also have significant benefits for managing animal health and end user compliance Extending the sustained release period from an intra-ruminal device using existing technology may result in increased variability of delivery or, in extreme cases, failure of the device function, for example, failure of the piston to move effectively at very low speed.

There is a need for intra-ruminal devices that allow for the sustained delivery of one or more actives to ruminant animals. It is an object of the present invention to go some way to meeting this need; and/or to at least provide the public with a useful choice.

SUMMARY OF THE INVENTION

In a first aspect the present invention may be said to broadly relate to an intra-ruminal device comprising a body substantially impervious to rumen fluid, the body comprising a barrel, at least one outlet, and at least one matrix in the barrel, a compression arrangement within the body adapted to bias the at least one matrix in the barrel to the at least one outlet, and at least one variable geometry device dependent from the body to assist rumen retention, wherein the at least one matrix in the barrel comprises at least one active ingredient and at least one clay mineral.

In a further aspect the present invention relates to a method of treating a ruminant animal in need thereof the method comprising administering the intra-ruminal device of the invention to a ruminant animal.

In a further aspect the present invention relates to a controlled delivery intra-ruminal device according to any one of claims 1 to 16, the method comprising granulating a mixture comprising at least one active ingredients, at least one clay mineral, and optionally one or more excipients, drying the granules, passing the granules through a sieve, and tabletting the granules into at least one matrix, and loading the at least one matrix into the body of an intra-ruminal device.

Preferably the device delivers an effective concentration of at least one active ingredient to a ruminant in need thereof.

Preferably the clay mineral is selected from the group consisting of kaolin, talc, nontronite, saponite, sepiolite, palygorskite, halloysite, vermiculite, muscovite, illite, hectorite, montmorillonite, bentonite, beidellite, volkonskoite, laponite, sauconite, magadiite, kanyaite, ledikite, nacrite, attapulgite, or zeolite, or a combination thereof.

Preferably the clay mineral is kaolin.

Preferably the clay mineral is present in an amount of 5-40% by weight of the matrix.

Preferably the device is for use in a method of treating a ruminant animal.

Preferably the device provides a sustained delivery of the one or more active ingredients over at least about 150 days.

Preferably the device provides a sustained delivery of the one or more active ingredients over at least about 250 days.

Preferably the device provides a sustained delivery of the one or more active ingredients over at least about 300 days.

Preferably the sustained delivery is substantially linear (>0.95).

Preferably the compression arrangement within the body is adapted to bias the at least one matrix in the barrel to the at least one outlet at a rate of about 0.1 to about 1.2 mm per day.

Preferably the compression arrangement within the body is adapted to bias the at least one matrix in the barrel to the at least one outlet at a rate of about 0.1 to about 0.8 mm per day.

Preferably the compression arrangement within the body is adapted to bias the at least one matrix in the barrel to the at least one outlet at a rate of about 0.2 to about 0.6 mm per day.

Preferably the at least one active ingredient is a nutritional supplement used to maximise productivity and/or animal health.

Preferably the at least one active ingredient is selected from the group consisting of parasiticides, non-steroidal anti-inflammatories, antibiotics, probiotics, antivirals, anthelmintics, steroid hormones, metabolic regulators, enzyme inhibitor, rumen methane inhibitors/regulators, ruminal fermentation modifiers, productivity regulators, vitamins and minerals, or a combination thereof.

Preferably the at least one active ingredient is a parasiticide.

Preferably the parasiticide is an anthelmintic selected from the group consisting of benzimidazoles, imidazothiazoles, tetrahydropyrimidines, macrocyclic lactones, salicylanides, substituted phenols, aromatic amides, isoquinolines, amino acetonitriles and spiroindoles, or a combination thereof.

Preferably the method delivers an effective concentration of at least one active ingredient to a ruminant in need thereof.

Preferably the method improve productivity of a ruminant.

Preferably the use of the device reduces the environmental impact of a ruminant.

Preferably the ruminant is selected from the group consisting of cattle, goats, sheep and deer.

Preferably the clay mineral is present in an amount of 5 to 40% by weight of the matrix.

Preferably the intra-ruminal device provides a sustained delivery of the one or more active ingredients over at least about 150 days.

Preferably the intra-ruminal device provides a sustained delivery of the one or more active ingredients over at least about 250 days. In some embodiments the at least one active ingredient in the intra-ruminal device is selected from the group consisting of analgesics, parasiticides, fermentation modifiers/regulators (for example, methane and nitrate inhibitors), anti-bloat agents, corticosteroids, antibiotics, anti-thyroid ingredients, antivirals, anthelmintics, steroid hormones, antihistamines, metabolic regulators, productivity regulators, vitamins and minerals, or a combination thereof.

Preferably the at least one active ingredient in the intra-ruminal device is an anthelmintic selected from the group consisting of isoxazolines, benzimidazoles, imidazothiazoles, tetrahydropyrimidines, macrocyclic lactones, salicylanides, substituted phenols, aromatic amides, isoquinolines, amino acetonitriles and spiroindoles, or a combination thereof.

Preferably the at least one outlet of the intra-ruminal device is located in a cap provided to one end of the body.

Preferably the intra-ruminal device is administered to a ruminant selected from the group consisting of cattle, goats, sheep and deer.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE FIGURES

The invention will now be described by way of example only and with reference to the drawings in which:

Figure 7:
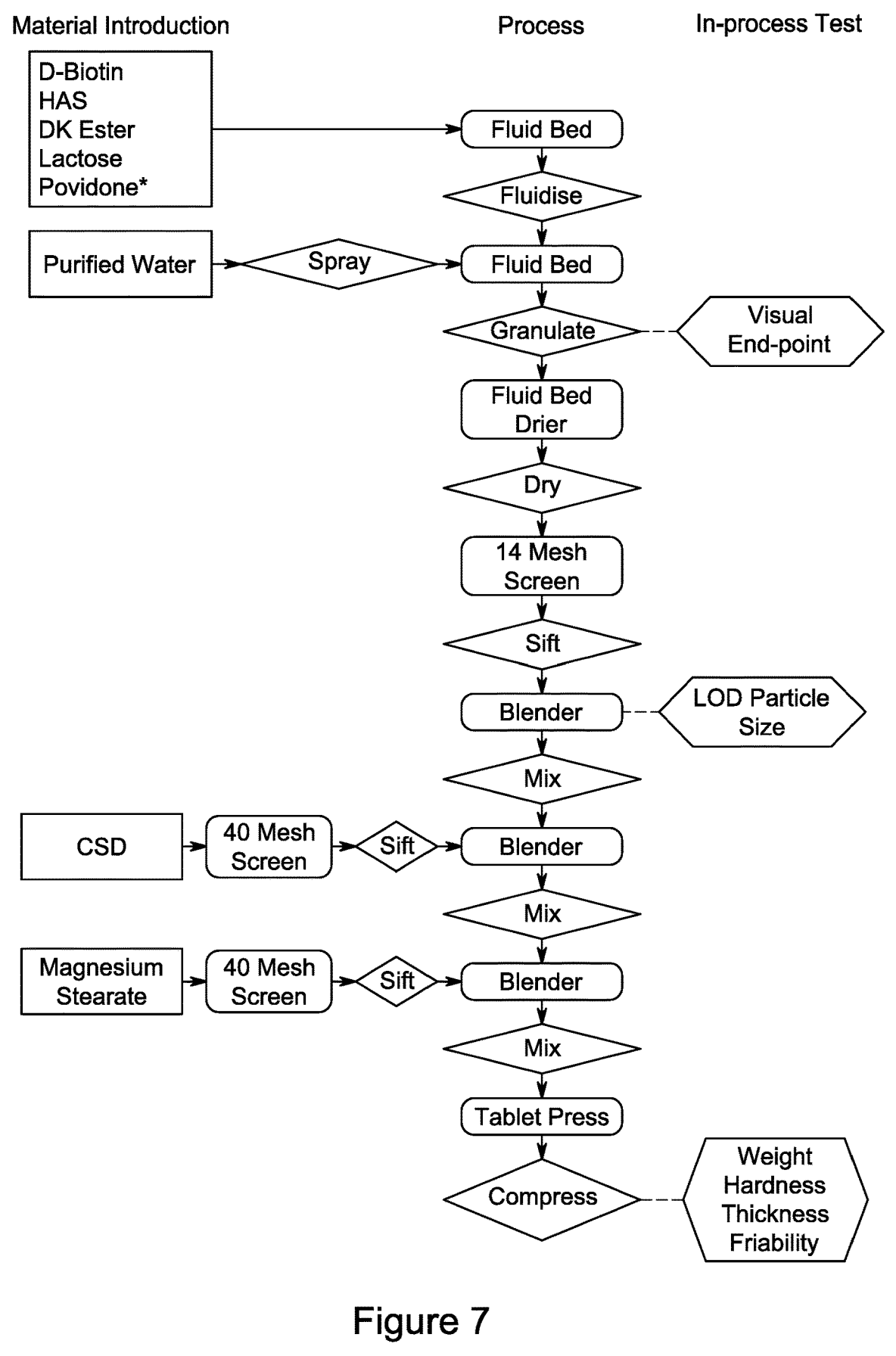

FIG. 7 is a flow chart showing the laboratory scale process for the manufacture of formulations F016 and F020, which are tablets as described in Example 4 herein. Note: Povidone was used for formulations F016, F017 and F020.

DETAILED DESCRIPTION OF THE INVENTION

Figure 1:
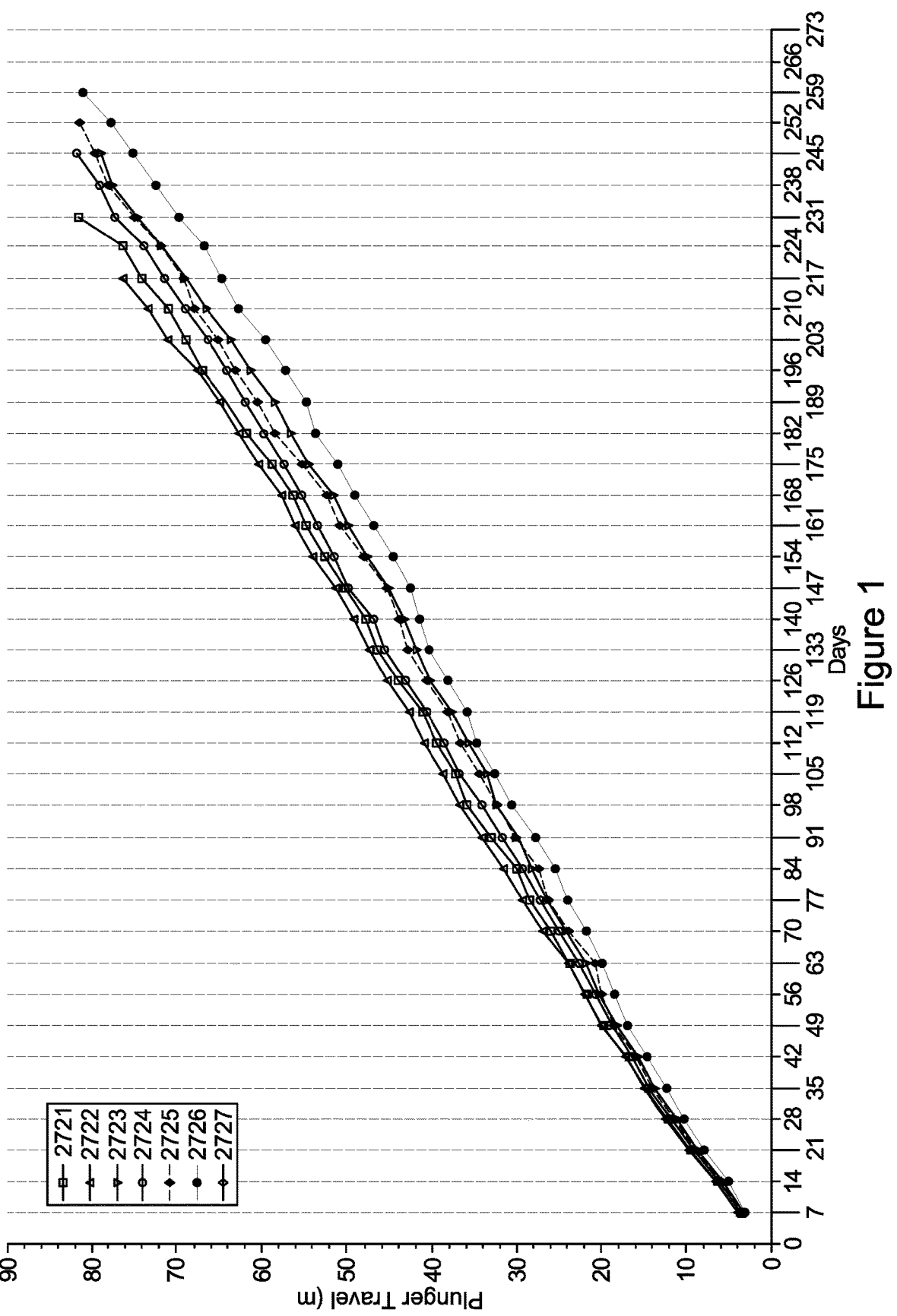
FIGS. 1 to 4 are graphs showing the payout period in days of biotin from four intra-ruminal devices Z721-Z727, Z763-Z769, Z770-Z776 and Z903-Z909 respectively when administered to fistulated cattle (n=7).
Figure 2:
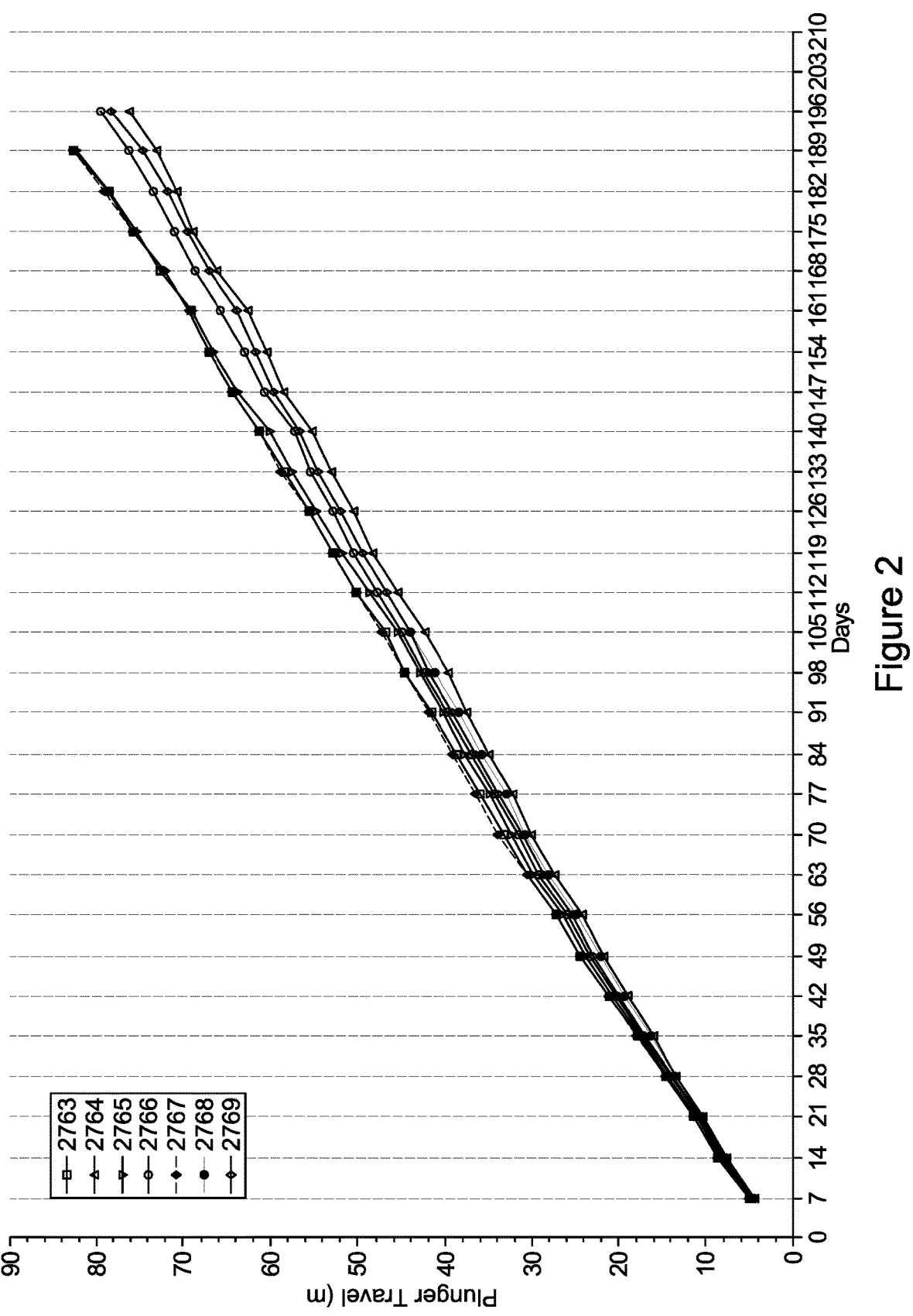

The present invention broadly relates to an intra-ruminal device for sustained, controlled release of one or more active ingredients to a non-human animal, preferably a ruminant animal.

1. Intra-Ruminal Device

The present invention relates to an intra-ruminal device, the device comprising a body substantially impervious to rumen fluid, the body comprising a barrel, at least one outlet, and at least one matrix in the barrel, a compression arrangement within the body adapted to bias at least one matrix in the barrel to the at least one outlet, and at least one variable geometry device dependent from the body to assist rumen retention, wherein the at least one matrix in the barrel comprises at least one active ingredient and at least one clay mineral.

The device of the invention may be used to deliver one or more active therapeutic or beneficial ingredients to a non-human animal. The non-human animal may be a ruminant animal, such as for example cattle, goats, sheep, deer, yaks and giraffes, preferably cattle or sheep.

In some embodiments, the body of the intra-ruminal device is rigid and holds its shape when the at least one matrix comprising the one or more active ingredients is inserted into the barrel of the device, and when the device is administered to an animal.

The body of the intra-ruminal device may be formed into a number of suitable shapes. Preferably the body of the intra-ruminal device is cylindrically shaped, and preferably the cross section of the body is circular. One end of the body may taper in to a reduced diameter to aid the passage of the intra-ruminal device down the oesophagus to the rumen.

The diameter of the body of the intra-ruminal device is small enough to pass down the oesophagus of a ruminant animal with ease and large enough to accommodate at least one matrix in the barrel. The diameter of the barrel depends on, for example the thickness of the body of the intra-ruminal device. In some embodiments the diameter of the intra-ruminal device and the diameter of the barrel may be very similar, the difference being the result of the thickness of the body.

In some embodiments the diameter of the intra-ruminal device may be less than about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, or 4.5 cm, and useful ranges may be selected from any of these values (for example the diameter of the intra-ruminal device may be from about 1 to about 4.5, about 1 to about 4 cm, from about 1 to about 3.5 cm, about 1 to about 3, about 1 to about 2.5, about 1 to about 2, about 1 to about 1.5, about 1.2 to about 4.5, about 1.2 to about 4, about 1.2 to about 3.5, about 1.2 to about 3, about 1.2 to about 2.5, about 1.2 to about 2, about 1.2 to about 1.5, about 1.5 to about 4.5, about 1.5 to about 3.5, about 1.5 to about 3, about 1.5 to about 2.5, or about 1.5 to about 2). The length of the body of the intra-ruminal device is short enough not to impede progress along the oesophagus to the reticulo-rumen.

The length of the body of the device can vary to, for example, accommodate more or fewer matrices. The length of the body may also vary depending on, for example, the target species to which the intra-ruminal device is to be administered, the size of the animal, the dose and pay-out period.

The length of the body may be from about 40, 45, 50, 55, 60, 65, 70, 75, 80, 85, 90, 95, 100, 105, 110, 115, 120, 125, 130, 135, 140, 145, 150, 155, 160, 165, 170, 175 or 180 mm or more, and useful ranges may be selected from any of these values (for example from about 40 mm to about 180 mm, 40 mm to about 150 mm, about 40 mm to about 120 mm, about 40 mm to about 100 mm, about 40 mm to about 75 mm, about 70 mm to about 180 mm, about 70 mm to about 160 mm, about 70 mm to about 160 mm, about 70 mm to about 140 mm, about 70 mm to about 120 mm, about 70 mm to about 100 mm, about 75 mm to about 180 mm, about 75 mm to about 165 mm, about 75 mm to about 145 mm, about 75 mm to about 125 mm, or about 75 mm to about 105 mm). For example in some embodiments the length of the body of an intra-ruminal device to be administered to sheep and other small ruminants may be from about 76 mm to about 90 mm, and the length of the body of the intra-ruminal device to be administered to cattle and other similar-sized ruminants may be from about 97 to about 170 mm.

In some embodiments, the body of the intra-ruminal device is impervious to intra-ruminal fluid but may allow permeation of gases. In some instances the permeability of the wall of the intra-ruminal device may require additional features to improve permeability of gasses and to prevent the formation of a partial vacuum above the compression arrangement that may affect smooth operation of the biasing system. The additional feature may include an aperture above the starting position of the compression arrangement that increases gas permeation but prevents or substantially prevents the ingress of ruminal fluids. This part of the intra-ruminal device may include an area of modified polymer or a vent incorporating a membrane such as a semi-permeable membrane.

In various embodiments the body of the intra-ruminal device may be made from a pharmaceutical grade polymer or co-polymer. Suitable polymers and co-polymers will be apparent to a person skilled in the art.

The intra-ruminal device comprises a retention means that serves to keep the device in the rumen and to prevent regurgitation. This may be achieved in a number of ways. For example the retention means may comprise a weighted component or part. The weighted component may be for example an area of the body that is made of a material of higher density than the material used to make the rest of the body. The weighted component may therefore ensure that the intra-ruminal device remains at the bottom of the rumen cavity to avoid regurgitation.

In various embodiments, the retention means may comprise a variable geometry device, preferably a retractable wing or pair of wings, preferably on one end of the body. The variable geometry device, preferably the wings, are pressed against the side of the body when administered and spring out after administration to prevent regurgitation. In some embodiments the intra-ruminal device may comprise more than one retention means, for example a variable geometry device such as a wing or pair of wings and one or more weighted components.

The variable geometry device, for example wings, may be pressed against the side of the body using a number of means. For example, water-soluble tape or adhesive may be used to hold the wings against the body.

In some embodiments the variable geometry device, for example wings, may be pressed against the side of the body by an applicator during dosing.

Figure 9:
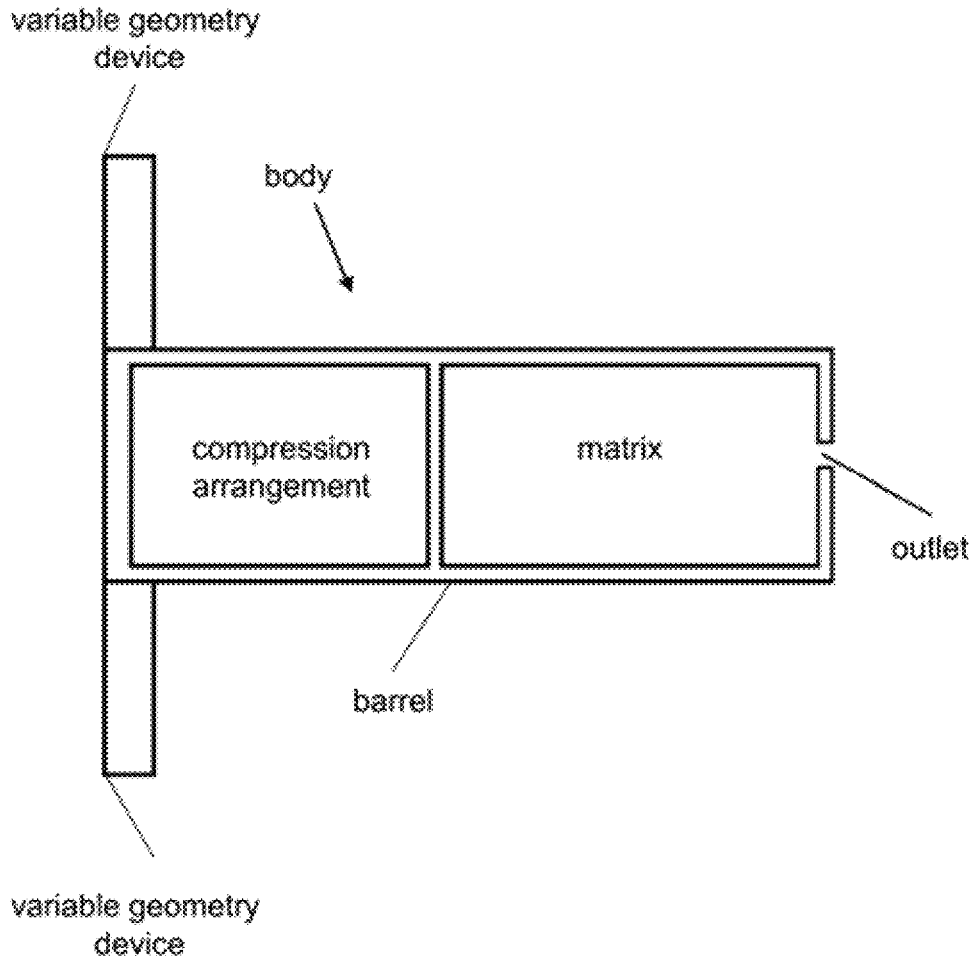
FIG. 9 is a schematic depiction of an intra-ruminal device.

FIG. 9 is a schematic depiction of an intra-ruminal device.

In some embodiments the variable geometry device, for example wings may be pressed against the side of the body using a pharmaceutical grade polymer or co-polymer that is readily dissolved by the contents of the rumen or using a polymer or co-polymer that melts at the temperature of the rumen, for example a polymer that melts at a temperature of from about 37.5, 38, 39, 39.5, 40, 40.5 or 41° C., and useful ranges may be selected from any of these values (for example from about 39 to about 40° C., or from about 38 to about 41° C.). Preferably the melting point of the polymer or co-polymer is from about 38.5 to about 40.5° C. to avoid the polymer melting in the oesophagus of the ruminant and releasing the wings from the side of the body before the device enters the rumen.

In some embodiments the variable geometry device, for example wings may be made from the same polymeric material as the body, or they may be made from a different polymeric material.

In various embodiments the variable geometry device, for example wings may be made of a polymeric material that is less rigid than the polymer used to make the body, to allow the wings to be retained against the side of the body during administration to an animal. Suitable polymeric materials will be apparent to a person skilled in the art and may include for example any pharmaceutical grade polymers that are sufficiently pliable to be held against the side of the intra-ruminal device when administered. In various embodiments the wings or part of the wings may be made of polypropylene or a co-polymer thereof.

In some embodiments, the body, and the variable geometry device, for example the wing(s) of the intra-ruminal device may be manufactured from one or more parts moulded from plastic materials (e.g. polypropylene) and may be fabricated together by adhesive and/or welding.

The intra-ruminal device comprises a compression arrangement located in the barrel of the device to compress the composition containing the active ingredient(s) towards the at least one outlet for release to the rumen. In various embodiments the at least one outlet is located at one end of the body and the compression arrangement biases the at least one matrix in the barrel of the intra-ruminal device towards the at least one outlet. The force exerted by the compression arrangement is intended to exceed any frictional forces generated between the core and the internal wall of the device over the entire distance that the compression arrangement travels to ensure consistent and linear delivery of the at least one matrix.

In some embodiments, the compression arrangement may comprise a plunger and biasing means. In various embodiments the biasing means may be a spring. In some embodiments, the biasing means, such as a spring, may be made of materials such as alloys of steel, for example stainless steel, carbon steel, oil tempered wire, chrome silicon steel or chrome vanadium steel. Other alloys may also be used, for example Inconel, Monel, beryllium, copper or phosphor bronze. Other suitable materials will be apparent to those skilled in the art.

In various embodiments the compression arrangement may be adapted to be extendible to at least about 45, 50, 55, 60, 65, 70, 75, 80, 85, 90, 95 or 100% of the length of the body, and suitable ranges may be selected from any of these values (for example from about 45 to about 100%, about 45 to about 75%, from about 45 to about 60%, about 50% to about 100%, about 60 to about 80%, about 50 to about 80%, about 50 to about 60%, about 60 to about 100%, about 60 to about 80%, about 70 to about 100%, about 70 to about 80%, or from about 80% to about 100%).

In exemplary embodiments the compression arrangement may comprise a spring that is adapted to push a plunger to extend the compression arrangement to at least about 80, 85, 90, 95 or 100% of the length of the body.

The pressure exerted by the compression arrangement, for example the biasing means such as a spring, remains substantially constant for the entire payout period, the substantially constant pressure leading to a linear or substantially linear (>0.95) sustained delivery of one or more active ingredients as described herein.

Without wishing to be bound by theory the inventors believe the pressure exerted by the compression arrangement, that is, the pressure biasing the at least one matrix towards the at least one outlet contributes to control of the payout period.

In various embodiments the barrel of the intra-ruminal device comprises at least one matrix comprising at least one active ingredient.

In some embodiments the barrel of the intra-ruminal device may comprise one matrix only or more than one matrix, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more matrices, and useful ranges may be selected from any of these values, for example 1 to 30 matrices, 1 to 25, 1 to 20 matrices, 1 to 15, 1 to 10 matrices, 1 to 5, 5 to 30, 5 to 25, 5 to 20, or 5 to 15 matrices.

The at least one matrix may be any shape adapted to fit inside the barrel of the device. In various embodiments the barrel of the intra-ruminal device may comprise more than one matrix. The form of the at least one matrix may be for example a tablet, a capsule, a caplet or a wafer.

In some embodiments the at least one matrix may be shaped to allow them to be stacked along the longitudinal axis of the body of the intra-ruminal device, such that they are sequentially presentable to the rumen, as originally proposed in the Laby device. Preferably the at least one matrix is a tablet, preferably disc-shaped.

In some embodiments the diameter of the at least one matrix may be less than about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 mm, and useful ranges may be selected from any of these values (for example the diameter of the matrices may be from about 9 to about 40 mm about 9 to about 30 mm, about 9 to about 20 mm, about 9 to about 10 mm, about 10 to about 35 mm, about 10 to about 25 mm, about 10 to about 15 mm, form about 11 to about 40, 11 to about 38, 11 to about 36, 11 to about 34, 11 to about 32 mm, 11 to about 30 mm, 11 to about 28 mm, 11 to about 26 mm, 11 to about 24 mm, 11 to about 22 mm, 11 to about 20 mm, 11 to about 19 mm, 11 to about 18 mm, 11 to about 17 mm, 11 to about 16 mm, 11 to about 15 mm, 11 to about 14 mm, 12 to about 40 mm, 12 to about 38, 12 to about 36, 11 to about 34, 12 to about 32 mm, 12 to about 30 mm, 12 to about 28 mm, 12 to about 26 mm, 12 to about 24 mm, 12 to about 22 mm, 12 to about 20 mm,)

For example in some embodiments the at least one matrix for use in intra-ruminal devices to be administered to sheep may be from about 11 to about 15 mm in diameter and the at least one matrix for use in intra-ruminal devices to be administered to cows may be from about 15 to about 32 mm in diameter.

The diameter of the at least one matrix comprising the one or more active ingredients must be such that the diameter is small enough to fit into the barrel of the device. For example if the diameter of the barrel of the device is 30 mm, then the matrix may have a diameter of for example around 29.5 mm. In various embodiments the diameter of the matrix may be sufficiently close to the internal diameter of the barrel to substantially prevent ingress of rumen fluid between the core and barrel without preventing movement of the matrix within the barrel.

In some embodiments the device may comprise a plurality of matrices, for example a plurality of compressed tablets, the number of matrices depending on the length of the body of the device, the thickness of the matrix, the desired payout period and the amount of active present in the at least one matrix. For example in some embodiments the thickness of the at least one matrix may be from at least about 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75 or 10 mm or more, and useful ranges may be selected between any of these values, for example from about 1 to about 10 mm, about 1 to about 8 mm, about 1 to about 6 mm, about 1 to about 4 mm, about 2 to about 10 mm, about 2 to about 8 mm, about 2 to about 6 mm, about 2 to about 4 mm, about 3 to about 10 mm, about 3 to about 9 mm, about 3 to about 7 mm, about 3 to about 5 mm, about 5 to about 10 mm, about 5 to about 9 mm, about 5 to about 8 mm, about 5 to about 7 mm, about 7 to about 10 mm, or from about 7 to about 9 mm.

In some embodiments the barrel may comprise one matrix only, for example one solid core comprising at least one active ingredient and optionally one or more excipients. In such embodiments the matrix may substantially span the length of the barrel from the compression arrangement to the end of the body comprising the at least one outlet.

In some embodiments the solid core may be continuous or constructed of individual compressed matrices or units (tablets) arranged in a stack.

The active ingredient(s) is released in to the rumen in a controlled manner by contact of the matrix comprising the active ingredient(s) with the intra-ruminal fluid allowing erosion or dissolution of the matrix in to the rumen.

A seal exists between the rumen-facing end of the matrix comprising the active ingredient(s) and the barrel of the intra-ruminal device. Without wishing to be bound by theory the inventors believe that an ineffective seal between the barrel and rumen-facing end of the matrix comprising the active ingredient(s) may allow other surfaces of the matrix or other matrices in the stack to swell, adversely affecting, or stopping reliable payout of the one or more active ingredients.

In various embodiments, the at least one outlet may be located at one end of the body. The outlet may be from about 1, 2, 3, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22 mm or more in diameter, and useful ranges may be selected in between any of these values (for example from about 1 to about 22 mm, about 1 to about 20 mm, about 1 to about 18.5 mm, about 1 to about 15 mm, about 1 to about 12 mm, about 1 to about 10 mm, about 1 to about 5 mm, about 3 to about 22 mm, about 3 to about 20 mm, about 3 to about 18.5 mm, about 3 to about 15 mm, about 3 to about 12 mm, about 4 to about 22 mm, about 4 to about 20 mm, about 4 to about 18.5 mm in diameter, about 4 to about 15 mm, or about 4 to about 12 mm). It will be understood by a person skilled in the art that the size of the outlets will depend on factors such as for example, the intended payout rate.

In various embodiments the diameter of the at least one outlet may be selected to ensure that a sufficient ridge exists to seal against the at least one matrix in the barrel of the intra-ruminal device.

In various embodiments, the intra-ruminal device comprises an end cap that contains the at least one outlet, provided to one end of the body. The end cap may be permanently fixed to the body of the intra-ruminal device, for example, it may be integral with the body of the intra-ruminal device.

Alternatively the end cap may be removably attached to the body of the intra-ruminal device.

In some embodiments the end cap may comprise one outlet only.

Alternatively the end cap may comprise more than one outlet, for example 2, 3, 4, 5, 6, 7, 8, 9, 10 or more outlets and useful ranges may be selected from any of these values, for example 2 to 6 outlets or 3 to 8 outlets. Preferably the one or more outlets are located at or near the centre of the end cap. Preferably if the end cap comprises multiple outlets then the outlets are substantially equidistant from one another.

In some embodiments, the end cap may be made of the same material as the body or a different material. In various embodiments the end cap is made of a polymeric material that is stable under the conditions present in the rumen of the animal.

The end cap, when present, may be secured to the end of the body by any suitable means. For example, the end cap may be welded or glued to the end of the barrel, preferably welded.

2. Matrix Contents

The intra-ruminal device of the invention comprises at least one matrix. The at least one matrix may comprise one or more active ingredients, one or more clay minerals and excipients in a ratio that allows for the delivery of a therapeutically effective amount of the one or more active ingredients to the non-human animal, preferably ruminant.

2.1 Clay Minerals

The inventors have advantageously discovered that the rate of release of nutritional or pharmaceutically active ingredient(s) from the at least one matrix in an intra-ruminal device may be modulated or controlled by the use of one or more clay minerals in the at least one matrix.

Clay minerals that may be used in the at least one matrix include phyllosilicates, such as for example kaolin, kaolinite [comprising hydrated aluminium silicate $(Al_2Si_2O_5(OH)_4)$], talc, nontronite, saponite, sepiolite, palygorskite, halloysite, vermiculite, muscovite, illite, hectorite, montmorillonite, bentonite, beidellite, volkonskoite, laponite, sauconite, magadiite, kanyaite, ledikite, nacrite, attapulgite, or zeolite. The matrices described herein may comprise one or more clay minerals.

In various embodiments at least one matrix may comprise one clay mineral, for example kaolin.

In various embodiments at least one matrix may comprise one clay mineral, for example kaolinite.

In various embodiments the at least one matrix may comprise hydrated aluminium silicate.

In some embodiments the clay mineral, for example kaolin, may be present in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more by weight of the matrix and useful ranges may be selected from any of these values (for example from about 1 to about 35%, or from about 5 to 40%, preferably from about 10 to about 35% by weight of the matrix).

In some embodiments more than one clay mineral may be present in the at least one matrix. For example in some embodiments 2, 3, 4 or 5 or more different clay minerals may be present. For example, in some embodiments kaolin may be present in the at least one matrix with 1, 2, 3, 4, or 5 or more other clay minerals.

In some embodiments the barrel may comprise more than one matrix and some of the matrices may comprise one or more clay minerals while others do not.

In some embodiments the barrel may comprise more than one matrix and some of the matrices may comprise one particular clay mineral while the remaining matrices comprise another clay mineral.

In some embodiments one or more clay minerals may be present in the at least one matrix in combination with one or more gel-forming polymers.

2.2 Active Ingredients

The at least one matrix in the intra-ruminal devices of the present invention delivers a therapeutic quantity of one or more active ingredients. The active ingredient(s) are delivered from the intra-ruminal device and may have a local action, for example in the gastrointestinal tract, and/or may have activity within the rumen including the microbial or enzymic environment, and/or they may be absorbed in to the systematic circulation to impart a therapeutic response in other body compartments including for example major organs and tissues.

A wide range of active ingredients may be delivered from the at least one matrix in the intra-ruminal devices of the present invention.

The intra-ruminal device of the invention comprises at least one matrix, the at least one matrix defining a core. In some embodiments the core may comprise a single therapeutic or a combination of blended therapeutics. In some embodiments the therapeutics may be separated throughout the core using individual matrices.

In some embodiments the at least one matrix may comprise one or more antibiotics, antifungals, antivirals, steroid hormones, antihistamines, metabolic regulators, for example rumen methane inhibitors/regulators, productivity regulators, corticosteroids, anti-thyroidal agents, parasiticides (ectoparasiticidal agents and/or endoparasiticidal agents), such as for example anthelmintics, non-steroidal anti-inflammatories, nutritional actives, ruminal fermentation modifiers, or a combination thereof.

In some embodiments the at least one matrix may comprise one or more vitamins, for example vitamin A, vitamin E, vitamin $B_{12}$, vitamin $B_3$, d-pantothenic acid (vitamin $B_5$), folic acid, vitamin $B_6$, vitamin $B_1$, vitamin $D_3$, vitamin C, vitamin $B_2$, vitamin $B_7$ or H. As another example, the nutritional active could be a pro-vitamin, for example beta-carotene or panthenol.

In some embodiments the nutritional active may be an amino acid. Suitable amino acids include but are not limited to the 20 naturally occurring L-amino acids, for example arginine, isoleucine, leucine, lysine, etc.

In some embodiments the nutritional active may be a co-enzyme, for example co-enzyme Q.

In some embodiments the nutritional active may be a mineral. Non-limiting examples of minerals include potassium, sodium, manganese, zinc, iron, calcium, copper, cobalt, iodine, chlorine and selenium. In some embodiments the mineral may be in the form of a suitable salt.

In some embodiments the at least one matrix may comprise one or more anti-microbial ingredients for example antibiotics, antifungals, antivirals, anthelmintics, and the like.

Suitable antibiotic agents may be those that act as inhibitors of cell wall synthesis (e.g. penicillins, cephalosporins, bacitracin and vancomycin), inhibitors of protein synthesis (aminoglycosides, macrolides, lincosamides, streptogramins, chloramphenicol, tetracyclines), inhibitors of membrane function (e.g. polymixin B and colistin), inhibitors of nucleic acid synthesis (e.g. quinolones, metronidazole, and rifampin), or inhibitors of other metabolic processes (e.g. anti-metabolites, sulfonamides, and trimethoprim). Non-limiting examples of antibiotics include polyethers, ionophores such as monensin and salinomycin, beta-lactams such as penicillins, aminopenicillins (e.g., amoxicillin, ampicillin, hetacillin, etc.), penicillinase resistant antibiotics (e.g., cloxacillin, dicloxacillin, methicillin, nafcillin, oxacillin, etc.), extended spectrum antibiotics (e.g., axlocillin, carbenicillin, mezlocillin, piperacillin, ticarcillin, etc.); cephalosporins (e.g., cefadroxil, cefazolin, cephalixin, cephalothin, cephapirin, cephradine, cefaclor, cefacmandole, cefmetazole, cefonicid, ceforanide, cefotetan, cefoxitin, cefprozil, cefuroxime, loracarbef, cefixime, cefoperazone, cefotaxime, cefpodoxime, ceftazidime, ceftiofur, ceftizoxime, ceftriaxone, moxalactam, etc.); monobactams such as aztreonam; carbapenems such as imipenem and eropenem; quinolones (e.g., ciprofloxacin, enrofloxacin, difloxacin, orbifloxacin, marbofloxacin, etc.); chloramphenicols (e.g., chloramphenicol, thiamphenicol, florfenicol, etc.); tetracyclines (e.g., chlortetracycline, tetracycline, oxytetracycline, doxycycline, minocycline, etc.); macrolides (e.g., erythromycin, tylosin, tlimicosin, clarithromycin, azithromycin, etc.); lincosamides (e.g., lincomycin, clindamycin, etc.); aminoglycosides (e.g., gentamicin, amikacin, kanamycin, apramycin, tobramycin, neomycin, dihydrostreptomycin, paromomycin, etc.); sulfonamides (e.g., sulfadmethoxine, sfulfamethazine, sulfaquinoxaline, sulfamerazine, sulfathiazole, sulfasalazine, sulfadiazine, sulfabromomethazine, suflaethoxypyridazine, etc.); glycopeptides (e.g., vancomycin, teicoplanin, ramoplanin, and decaplanin; and other antibiotics (e.g., rifampin, nitrofuran, virginiamycin, polymyxins, tobramycin, etc.).

In some embodiments the at least one matrix may comprise one or more antifungal active ingredients for example one or more polyenes, azoles, allylamines, morpholines, antimetabolites, and combinations thereof. For example in some embodiments the at least one matrix may comprise one or more of fluconazole, itraconazole, clotrimazole, ketoconazole, terbinafine, 5-fluorocytosine, and amphotericin B, or combinations thereof.

Non-limiting examples of antivirals that may be present in the at least one matrix may include didanosine, lamivudine, stavudine, zidovudine, indinavir, and ritonavir.

In some embodiments the at least one matrix may comprise one or more steroid hormone, for example steroid hormones such as growth promoters and production enhancers. In some embodiments, the steroid hormone may be natural steroid hormone, such as for example estradiol, progesterone, and testosterone, or a synthetic steroid hormone, such as trenbolone acetate, estradiol benzoate, estradiol 17ß, and melengestrol acetate, and/or zeranol.

Steroid hormones that may be present in at least one matrix may comprise for example natural and synthetic steroid hormones, steroid hormone precursors, steroid hormone metabolites, and derivatives thereof that are structurally derived from cholesterol. Steroid hormones may be synthesized from cholesterol via pathways that involve cytochrome P450 (cP450) enzymes, which are heme-containing proteins.

In some embodiments the at least one matrix may comprise one or more steroid hormones such as for example androgens, estrogens, progestogens, mineral corticoids, and glucocorticoids. Exemplary androgens include, but are not limited to, testosterone, dehydroepiandrosterone, dehydroepiandrosterone sulphate, dihydrotestosterone, androstenedione, androstenediol, androstanedione, androstanediol, and any combination thereof. Exemplary estrogens include, but are not limited to, estrone, estradiol, estriol, estetrol, equilin, equilenin, and any combination thereof. Exemplary progestogens include, but are not limited to, progesterone, 17-hydroxy-progesterone, pregnenolone, dihydroprogesterone, allopregnanolone, 17-hydroxy-pregnenolone, 17-hydroxy-dihydroprogesterone, 17-hydroxy-allopregnanolone, and any combination thereof. Exemplary mineralcorticoids include, but are not limited to, aldosterone, 11-deoxycorticosterone, fludrocortisones, 11-deoxy-cortisol, pregnenedione, and any combination thereof. Exemplary glucocorticoids, include, but are not limited to, cortisol (hydrocortisone), corticosterone, 18-hydroxy-corticosterone, cortisone, and any combination thereof.

In some embodiments the at least one matrix may comprise one or more anti-histamines, such as for example clemastine, clemastine fumarate (2(R)-[2-[1-(4-chlorophenyl)-1-phenyl-ethoxy]ethyl-1-methylpyrrolidine), dexmedetomidine, doxylamine, loratidine, desloratidine and promethazine, and diphenhydramine, or pharmaceutically acceptable salts, solvates or esters thereof.

In some embodiments the at least one matrix may comprise one or more active ingredients that are adapted to modify intra-ruminal fermentation processes.

In some embodiments the at least one matrix may comprise one or more metabolic regulators, such as for example one or more methane inhibitors/regulators, or fermentation regulators/modifiers. In some embodiments the at least one matrix may comprise one or more productivity regulators, for example polyethers such as monensin. In some embodiments, the productivity regulator may be a productivity enhancer.

In exemplary embodiments the at least one matrix may comprise one or more anthelmintic agents, for example one or more benzimidazoles, imidazothiazoles, tetrahydropyrimidines, macrocyclic lactones, salicylanilides, substituted phenols, aromatic amides, isoquinolines, amino acetonitriles, spiroindoles, isoxazolines, or combinations thereof.

Anthelmintic benzimidazoles comprise for example mebendazole, flubendazole, fenbendazole, oxfendazole, oxibendazole, albendazole, albendazole sulfoxide, thiabendazole, thiophanate, febantel, netobimin, and triclabendazole. Further examples include mebendazole, and ricobendazole.

Without wishing to be bound by theory, the inventors believe that benzimidazole-based anthelmintics may interfere with the worm's energy metabolism on a cellular level by binding to a specific building block called beta tubulin and preventing its incorporation into certain cellular structures called microtubules, which are essential for energy metabolism.

Imidazothiazoles and tetrahydropyrimidines are both nicotinic agonists. In some embodiments the one or more anthelmintic agents in at least one matrix may comprise imidathiazoles, for example levamisole, tetramisole, and butamisole. Tetrahydropyrimidine anthelmintics that may be used in the matrices of the invention include, for example, morantel, oxantel, and pyrantel.

Without wishing to be bound by theory the inventors believe that tetrahydropyrimidines may mimic the activity of acetylcholine, a naturally occurring neurotransmitter that initiates muscular contraction. This may lead to helminths that are unable to feed and starve.

Without wishing to be bound by theory the inventors believe that imidazothiazoles may have a similar mode of action to tetrahydropyrimidines and may cause spastic paralysis of helminths, For example, levamisole is thought to have a broad spectrum of activity and may therefore be effective against many larval stages of parasites.

In various embodiments the at least one matrix may comprise one or more macrocyclic lactones, for example abamectin, doramectin, eprinomectin, ivermectin, selamectin, milbemycin, for example as milbemycin oxime, moxidectin or a combination thereof.

In some embodiments the at least one matrix may comprise one or more salicylanilides for example brotianide, clioxanide, closantel, niclosamide, oxyclozanide, rafoxanide, substituted phenols including for example bithionol, disophenol, hexachlorophene, niclofolan, menichlopholan, nitroxynil, and aromatic amides, including for example diamfenetide (diamphenethide) or combinations thereof.

In some embodiments the at least one matrix may comprise one or more isoquinoline anthelmintics, such as for example praziquantel and epsiprantel. In some embodiments the matrices of the invention and the intra-ruminal devices may comprise one or more amino-acetonitrile derivatives, such as for example monepantel.

In some embodiments the at least one matrix may comprise one or more active ingredients such as for example piperazine and derivatives thereof such as piperazine and diethylcarbamazine (DEC, a derivative of piperazine), benzenesulfonamides such as clorsulon, amidines such as bunamidine, isothiocyantes such as nitroscanate, and organophosphates such as dichlorvos, and spiroindoles such as derquantel (2-deoxoparaherquamide).

In various embodiments, the one or more active ingredient(s) in the at least one matrix of the intra-ruminal device, is/are stable and do not react with other components in the at least one matrix or degrade or decompose by other means.

In various embodiments, the payout rates of the active ingredient(s) may be measured as a function of the width of a matrix ejected into the rumen through the one or more outlets in the end cap. In some embodiments the payout rate of the intra-ruminal device of the invention may be from about 0.1, 0.125, 0.15, 0.175, 0.2, 0.225, 0.025, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, or 1.2 mm or more per day in an aqueous medium, for example ruminal fluid or water, and suitable ranges may be selected from any of these values, for example from about 0.1 to about 1.2, about 0.1 to about 1, about 0.1 to about 0.75, 0.1 to about 0.6, 0.1 to about 0.5, 0.2 to about 1.2, about 0.2 to about 0.75, about 0.2 to about 0.6, about 0.2 to about 0.5 mm/day. It will be understood by a person skilled in the art that the payout rate as a function of the width of a matrix may depend on the size of the intra-ruminal device.

Preferably, the payout of the one or more active ingredients is linear or substantially linear. In various embodiments the linearity may be greater than from about 0.95, 0.955, 0.96, 0.965, 0.97, 0.975, 0.98, 0.985, 0.99, 0.995, 0.996, 0.997, 0.998, 0.999 or more and suitable ranges may be selected from any of these values, for example from about 0.95 to about 0.999, from about 0.99 to about 0.995, from about 0.99 to about 0.996, from about 0.99 to about 0.997, from about 0.99 to about 0.998, from about 0.99 to about 0.999.

In various embodiments, the payout rates of the one or more active ingredient(s) is/are minimally affected, preferably not affected by the pH and ionic composition of the rumen.

In some embodiments, the at least one matrix of the intra-ruminal device, may comprise more than one active ingredient. For example in some embodiments the matrices of the invention may comprise from 2, 3, 4, 5, 7, 8, 9, or about 10, or more active ingredients, and useful ranges may be selected from any of these values (for example from 2 to about 10 or from 2 to about 5 active ingredients).

In some embodiments the at least one matrix may comprise more than one active ingredient, wherein some or all of the active ingredients belong to a different therapeutic class, for example antibiotics, antifungals, antivirals, steroid hormones, antihistamines, metabolic regulators, productivity regulators, corticosteroids, anti-thyroidal agents, parasiticidal agents, such as for example anthelmintics and/or nutritional actives. For example the matrix may comprise 3 actives, one of which is an anthelmintic, one of which is an antibiotic and the third being a nutritional active, for example a vitamin. In various embodiments the at least one matrix of the intra-ruminal device may comprise more than one active ingredient, each of which belongs to the same therapeutic class, preferably anthelminitics. In some embodiments the matrix may comprise two or more anthelmintic actives belonging to the same class of anthelmintics, such as for example benzimidazoles, imidazothiazoles, tetrahydropyrimidines, macrocyclic lactones, salicylanilides, substituted phenols, aromatic amides, isoquinolines, amino acetonitriles and spiroindoles. For example the at least one matrix may comprise two or three actives, each of which may be a macrocyclic lactone.

In various embodiments the at least one matrix of the intra-ruminal device may comprise two or more active ingredients each of which is an anthelmintic active and each belonging to a different anthelmintic class, such as for example benzimidazoles, imidazothiazoles, tetrahydropyrimidines, macrocyclic lactones, salicylanilides, substituted phenols, aromatic amides, isoquinolines, amino acetonitriles and spiroindoles. For example the matrices may comprise two anthelmintics, one of which may be a macrocyclic lactone and the other may be an imidazothiazole.

In some embodiments the at least one matrix may comprise at least about 5, 7.5, 10, 12.5, 15, 17.5, 20, 22.5, 25, 27.5, 30, 32.5, 35, 37.5, 40, 42.5, 45, 47.5, 50, 52.5 or 55% or more of one or more active ingredients by weight of each matrix, and useful ranges may be selected from any of these values (for example from about 5 to about 55, about 5 to about 50, about 5 to about 25, about 5 to about 10, about 6 to about 55, about 6 to about 50, about 6 to about 25, about 6 to about 10, about 7 to about 55, about 7 to about 50, about 7 to about 35, about 7 to about 10, about 8 to about 55, about 8 to about 50% about 8 to about 50, about 8 to about 25, about 8 to about 10, about 9 to about 55, about 9 to about 50, about 9 to about 25, about 10 to about 55, about 10 to about 50, about 10 to about 40, about 10 to about 30, about 10 to about 25, or about 10 to about 25% by weight of the matrix).

In various embodiments the matrix (tablet(s)) of the invention and the intra-ruminal devices comprising these tablets comprise a ratio of one or more active ingredients, clay(s) and other ingredients that allows for the delivery of a therapeutically effective amount of the one or more active ingredients to the non-human animal, preferably ruminant.

2.3 Other Ingredients

The at least one matrix comprising the one or more active ingredients and one or more clay minerals may further comprise a number of excipients. Examples of suitable excipient may include, but are not limited to fillers, diluents, lubricants, surfactants, glidants, gel formers, binders, and stabilisers, or combinations thereof.

In some embodiments, the at least one matrix of the invention may further comprise one or more fillers or diluents. Examples of suitable fillers or diluents may include, but are not limited to, sugars such as for example lactose, sucrose and mannitol, inorganic salts such as calcium phosphate and calcium carbonate, cellulose, methyl cellulose, ethyl cellulose, aluminium silicates, kaolin or combinations thereof.

In some embodiments the at least one matrix may comprise one or more fillers and/or diluents at amounts of from about 0, 0.1, 0.25, 0.5, 0.75, 1, 2, 3, 4, 5, 6, 7, 8, 9, 10, 12.5, 15, 17.5, 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95% by weight of the matrix, and useful ranges may be selected from any of these values (for example from about 0.1 to about 95, 0.1 to about 80, 0.1 to about 50, 0.1 to about 20, 0.1 to about 15, 0.1 to about 10, 0.1 to about 5, 5 to about 95, 5 to about 90, 5 to about 75, 5 to about 50, 5 to about 25, or about 5 to about 10% by weight of the matrix).

For example, in some embodiments the filler/diluent may comprise lactose and/or another filler such as for example sucrose or mannitol, or combinations thereof in an amount of about 0.1 to about 35% of the matrix.

In some embodiments the filler/diluent may comprise cellulose or a cellulose derivative such as for example, methyl cellulose and/or ethyl cellulose, or a combination of any two or more thereof, with or without the presence of one or more other fillers/diluents, in an amount of about 0.1 to about 80% by weight of the matrix.

In some embodiments the filler/diluent may comprise a filler/diluent selected from the group consisting of aluminium silicates, kaolin, calcium phosphate and calcium carbonate, or a combination of any two or more thereof, with or without the presence of one or more other fillers/diluents, in an amount of about 0.1 to about 80% by weight of the matrix.

In some embodiments, the at least one matrix may comprise one or more surfactants or lubricants. Examples of surfactants or lubricants may include, but are not limited to, stearates such as for example magnesium stearate, calcium stearate, and stearyl fumarate, glyceryl stearates such as for example glyceryl monostearate, glycerine derivatives, sodium lauryl sulfate, sucrose fatty acid ester, polyoxamer, mineral clays such as for example kaolin, aluminium silicate or combinations thereof. In some embodiments the one or more surfactants and/or lubricants may be present in the matrices of the invention in an amount of from about 0.01, 0.05, 0.075, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, or 90% by weight of the matrix, and useful ranges may be selected from any of these values (for example from about 0.01 to about 90, about 0.01 to about 75, about 0.01 to about 50, about 0.01 to about 25, about 0.01 to about 10, about 0.5 to about 90, about 0.5 to about 75, about 0.5 to about 50, about 0.5 to about 25, about 5 to about 80, about 5 to about 60, about 5% to about 40, or about 5 to about 20%).

For example, in some embodiments the lubricant/surfactant may comprise stearates such as for example magnesium stearate or calcium stearate, stearyl fumarate, glyceryl stearates such as for example glyceryl monostearate, glycerine derivatives or combinations thereof, in an amount of about 0.05 to about 3% by weight of the matrix.

In some embodiments the lubricant/surfactant may comprise sodium lauryl sulfate in an amount of about 0.01 to about 5% by weight of the matrix.

In some embodiments the lubricant/surfactant may comprise one or more sucrose fatty acid esters in an amount of about 5 to about 80% by weight of the matrix.

In some embodiments the lubricant/surfactant may comprise one or more poloxamers in an amount of about 0.01 to about 10% by weight of the matrix.

In some embodiments the lubricant/surfactant may comprise one or more fillers such as one or more mineral clays and/or aluminium silicates, such as for example kaolin in an amount of about 0.1 to about 80% by weight of the matrix.

In some embodiments, the at least one matrix may further comprise one or more glidants. Examples of glidants include, but are not limited to, colloidal silicon dioxide, talc, metal stearates such as magnesium stearate, calcium stearate and stearyl fumarate, and glyceryl stearates such as glyceryl monostearate, or combinations thereof.

In some embodiments the glidant(s) may be present in the at least one matrix in amounts of from about 0.01, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5% by weight of the matrix, and useful ranges may be selected from any of these values (for example from about 0.01 to about 5, about 0.01 to about 4, about 0.01 to about 2, about 0.01 to about 1, about 0.25 to about 5, about 0.25 to about 4, about 0.25 to about 3, about 0.25 to about 1, about 0.5 to about 5, about 0.5 to about 3, about 0.5 to about 2, about 0.5 to about 1% weight of the matrix).

In some embodiments the glidant may comprise colloidal silicon dioxide, talc, metal stearates such as magnesium stearate, calcium stearate and stearyl fumarate, and/or glyceryl stearates such as glyceryl monostearate, or combinations thereof in an amount of about 0.01 to about 2% by weight of the matrix.

In some embodiments, the at least one matrix may comprise one or more additional gel formers. Examples of additional gel formers that may be used include, but are not limited to, sucrose fatty acid ester, cellulosic derivatives such as hydroxyethyl cellulose and hydroxymethyl cellulose, and chitosan, or combinations thereof.

The gel former(s) may be present in the at least one matrix in amounts of from about 0.1, 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 10, 15, 20, 25, 30, 35, 40, 45, 50, 55, 60, 65, 70, 75, 80, 85 or 90% by weight of the matrix, and useful ranges may be selected from any of these values (for example from about 0.1 to about 90, about 0.1 to about 80, about 0.1 to about 50, about 0.1 to about 20, about 0.1 to about 15, about 0.1 to about 10, about 0.5 to about 90, about 0.5 to about 80, about .5 to about 50, about 0.5 to about 30, about 0.1 to about 5, about 5 to about 90, about 5 to about 75, about 5 to about 50, about 5 to about 25, or about 5 to about 10% by weight of the matrix).

In some embodiments the gel former may comprise sucrose fatty acid ester in an amount of about 5 to about 80% by weight of the matrix.

In some embodiments the gel former may comprise one or more poly(ethylene) oxides in an amount of about 0.1 to about 90% by weight of the matrix.

In some embodiments the gel former may comprise one or more polyacrylic acid polymers, for example Carbomers, in an amount of about 0.01 to about 15% by weight of the matrix.

In some embodiments the at least one matrix may comprise one or more polymers, for example one or more non-ionic polymers and/or one or more cross-linked anionic polymers. In some embodiments the one or more polymers may be one or more polyethylene oxides and/or polyvinylpyrrolidone.

In some embodiments the gel former may comprise one or more cellulosic derivatives, for example hydroxyethyl cellulose and hydroxymethyl cellulose, or a combination thereof in an amount of about 0.01 to about 90% by weight of the matrix.

In some embodiments the gel former may comprise cellulose in an amount of about 0.01 to about 30% by weight of the matrix.

In some embodiments, the at least one matrix may comprise one or more binders. Examples of binders include, but are not limited to, polyvinylpyrrolidone, cellulosic derivatives such as hydroxyethyl cellulose and hydroxymethyl cellulose.

The binder(s) may be present in the at least one matrix in amounts of from about 0, 0.1, 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 10, 15, 20, 25, 30, 35, 40, 45, or 50% by weight of the matrix, and useful ranges may be selected from any of these values (for example from about 0.1 to about 50, about 0.1 to about 35, about 0.1 to about 10, about 0.1 to about 10, about 0.5 to about 50, about 0.5 to about top 25, about 0.5 to about 10, about 0.5 to about 5, about 1 to about 50, about 1 to about 35, about 1 to about 20, about 1 to about 10, or about 1 to about 5% by weight of the matrix).

In some embodiments the binder may comprise polyvinylpyrrolidone in an amount of about 0.01 to about 10% by weight of the matrix.

In some embodiments the binder may comprise one or more cellulosic derivatives, for example methyl and/or ethyl cellulose, or a combination thereof in an amount of about 0.01 to about 35% by weight of the matrix.

In some embodiments, the at least one matrix may comprise one or more stabilisers. Examples of stabilisers that may be used in the matrices include, but are not limited to, antioxidants such as for example butylated hydroxytoluene, butylated hydroxyanisole and tocopherol, and/or buffers.

The stabilisers(s) may be present in the at least one matrix in amounts of from about 0.01, 0.02, 0.03, 0.04, 0.05, 0.06, 0.07, 0.08, 0.09, 0.1, 0.15, 0.2, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5% by weight of the matrix, and useful ranges may be selected from any of these values (for example from about 0.01 to about 5, about 0.01 to about 3, about 0.01 to about 1, about 0.01 to about 5, 0.1 to about 5%, about 0.5 to about 3.5% by weight of the matrix).

In some embodiments the stabiliser may comprise one or more chemical stabilizers. For example, in some embodiments the stabiliser may comprise one or more antioxidants such as for example butylated hydroxytoluene, butylated hydroxyanisole and tocopherol, or combinations thereof in an amount of about 0.01 to about 10% by weight of the matrix.

In some embodiments the stabiliser may comprise one or more buffers in an amount of 0.1 to about 5% by weight of the matrix. Suitable buffers will be known to a person skilled in the art.

In some embodiments the at least one matrix may comprise lactose, magnesium stearate and a sucrose fatty acid ester as excipients.

In some embodiments the one or more matrix matrices comprise lactose in an amount of from about 0.1 to about 35%, magnesium stearate in an amount of from about 0.05 to about 3.0% and sucrose fatty acid ester in an amount of from about 5 to 80%.

In some embodiments the at least one matrix may comprise lactose, magnesium stearate, a sucrose fatty acid ester and colloidal silicon dioxide as excipients.

In some embodiments the at least one matrix may comprise lactose in an amount of from about 0.1 to about 35%, magnesium stearate in an amount of from about 0.05 to about 3.0% and sucrose fatty acid ester in an amount of from about 5 to 80% and colloidal silicon dioxide in an amount of from about 0.01 to about 2.0% by weight of the matrix.

3. Method of Manufacture

In some embodiments the present invention provides a method of manufacturing an intra-ruminal device as described herein.

In some embodiments the method comprises
granulating a mixture comprising at least one active ingredients and at least one clay mineral, and optionally one or more excipients as described herein,
drying the granules,
passing the granules through a sieve, and
tabletting/compressing the granules into at least one matrix, and
loading the at least one matrix into the body of an intra-ruminal device.

The granulated mixture may be prepared by wet or dry granulation and it will be apparent to a person skilled in the art that a number of granulation processes may be used. For example, the mixture may be prepared by wet granulation using a high-shear granulator, a fluidized bed granulator or by any other suitable means known to a person skilled in the art.

In some embodiments the mixture may be granulated in a fluid-bed drier, for example by wet granulation comprising spraying a pharmaceutically acceptable solvent, for example water or a suitable alcohol or glycol ether onto the material to be granulated.

It will be understood by a person skilled in the art that pre-tabletting/compression processes other than fluid-bed granulation may be used. For example direct blending or other wet or dry granulation processes may be used.

In some embodiments the at least one matrix may be manufactured using a fluid-bed granulation process prior to the tablet compression process. In some embodiments a single stroke or a rotary tablet press may be used.

In various embodiments the matrices may undergo granulation or blending prior to compression.

In some embodiments granulation may comprise high shear mixing and/or roller compaction.

The at least one matrix of the invention may be compressed as flat-faced compacts, which means the matrices do not have limited or no curvature or edge bevel. The flat-faced matrices formed in this way may allow a continuous stack of matrices to be formed when assembled in the intra-ruminal device.

In some embodiments, the processing parameters such as air velocity, atomising air pressure and/or spray rate may be adjusted in order to provide granules of the desired attributes.

In some embodiments the air velocity used for granulation may be from at least about 2, 3, 4, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 Pa or more, and useful ranges may be selected from any of these values (for example from about 2 to about 24, about 2 to about 30, about 2 to about 28, about 2 to about 26, about 2 to about 24, about 2 to about 22, about 2 to about 20, about 2 to about 18, about 2 to about 16, about 2 to about 14, about 2 to about 12, about 2 to about 10, about 5 to about 45, about 5 to about 40, about 5 to about 20, about 5 to about 10 Pa).

In some embodiments the atomising air pressure may be from at least about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 bar or more, and useful ranges may be selected from any of these values (for example from about 0.5 to about 5.0, about 0.5 to about 2.5, about 0.5 to about 1.0, about 1.0 to about 5.0, about 1.0 to about 4, about 1.0 to about 3.0, about 1.0 to about 2.0, about 2.0 to about 5.0, or from about 2.0 to about 4.0 bar).

In some embodiments the spray rate may be from at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 g/min or more, and useful ranges may be selected from any of these values (for example from about 5 to about 50, about 5 to about 30, about 5 to about 10, about 20 to about 50, about 20 to about 40, or about 20 to about 20 g/min).

In one embodiment the batches are dried at from about 20, 21, 22, 23, 24, 25, 26, 27, 28, 29, 30, 31, 32, 33, 34, 35, 36, 37, 38, 39, 40, 41, 42, 43, 44, or 45° C., and suitable ranges may be selected from any of these values (for example from about 20 to about 45, about 20 to about 30, about 25 to about 45, about 25 to about 35, about 30 to about 45 or about 30° C. to about 35° C.).

In some embodiments the batches may be dried for at least about 0.5, 1, 2, 3, 4, 5, 6, 7, 8, 9, 10, 12, 14, 16, 18, 20, 22, 24, 30, 36, 42 or 48 hours or more, and suitable ranges may be selected from any of these values (for example at least about 0.5 to 48, about 0.5 to about 24, about 0.5 to about 12, about 0.5 to about 6, about 1 to about 48, about 1 to about 24, about 1 to about 12, about 1 to about 6, or about 1 to about 5 hours).

In some embodiments the batches may be dried to a defined granule moisture level, for example batches may be dried until a loss on drying (LoD) value of at least about 1, 1.25, 1.5, 1.75, 2, 2.25, 2.5, 2.75, 3, 3.25, 3.50, 3.75, 4, 4.25, 4.5, 4.75, or 5% weight by weight (w/w) is achieved, and useful ranges may be selected from any of these values, for example from about 1 to about 5, about 1 to about 3, about 1.5 to about 5, about 1.5 to about 4, about 1.5 to about 3% w/w.

In some embodiment the dried granules may be passed through a sieve, for example a 14 mesh sieve.

The above parameter ranges will apply when a Glatt GPCG 1 fluid bed drier is used. It will be understood by a person skilled in the art that a number of other machinery may be used and that the machinery used will affect the processing parameters described above. It will also be apparent to a person skilled in the art that the above fluid bed drier may be used for small-scale manufacture only. Methods for scaling up the granulation processes including suitable machinery will be apparent to a person skilled in the art.

The resulting granules may then be tabletted, for example using any suitable tablet press. In some embodiments the granules may be tabletted using a single stroke press or a rotary tablet press.

In various embodiments the matrices may be packaged for use in an intra-ruminal device.

In some embodiments at least one matrix may be loaded in to an intra-ruminal device. In some embodiments the at least one matrix may be loaded into an intra-ruminal device manually or the loading step may be automated and performed by one or more machines.

4. Use of the Composition

The at least one matrix and intra-ruminal device when used together may be capable of delivering a therapeutically effective amount of a range of active ingredients, such as for example anthelmintics, to non-human animals, preferably ruminants. The intra-ruminal device may deliver the active to the rumen by diffusion through the at least one outlet in one end of the intra-ruminal device.

In various embodiments the intra-ruminal device comprising the one or more active ingredients may be used for treating an animal in need thereof. The suitability of the intra-ruminal device of the invention for treating a particular disease or condition, depends for example on the active ingredients present in the composition.

In various embodiments the intra-ruminal device comprising the one or more active ingredients may be used to improve productivity, for example by improving growth and protein yield.

In various embodiments the intra-ruminal device comprising the one or more active ingredients may be used to minimise the impact of a production animal, for example a ruminant, on the environment, for example by reducing greenhouse gas emissions and/or nitrates.

The term "treatment", and related terms, such as "treating" and "treat" as used herein, relates generally to treatment, of a non-human animal, to achieve one or more desired therapeutic effects. The therapeutic effect may be, for example, the inhibition of progress of a disease or condition, including a reduction in the rate of progress, a halt in the rate of progress, amelioration, and/or cure. Treatment as a prophylactic measure is also contemplated. Treatment may comprise combination treatments and therapies, in which two or more treatments or therapies are used, for example, sequentially or simultaneously, in combination.

In various embodiments the present invention may also provide a method of treating a non-human animal, preferably a ruminant, in need thereof, the method comprising administering a therapeutically effective amount of one or more active ingredients in the form of the at least one matrix in an intra-ruminal device as described herein.

A person skilled in the art will be able to readily determine the appropriate dosage required to treat an animal suffering from one or more conditions and/or to prevent one or more conditions. The dosage will depend upon the active ingredient(s) present in the composition and may also depend on the frequency of administration, the sex, age, weight and general condition of the animal treated, the nature and severity of the condition treated, any concomitant diseases to be treated, and any other factors which will be evident to those skilled in the art.

In some embodiments, the intra-ruminal device may provide a sustained delivery of one or more nutritional and/or pharmaceutically active ingredients over an extended period of time. In some embodiments, the one or more active ingredients may be delivered over a payout period of from about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 275, 300, 205, 310, 325, 320, or 330 days or more, and useful ranges may be chosen from any of these values, for example from about 20 to about 250 days, or from about 100 to about 300 days. In some embodiments the intra-ruminal device may provide a sustained delivery over more than 330 days, the payout limited period being limited only by the length of the intra-ruminal device.

The inventors believe that the sustained release effect (pay-out period) from an intra-ruminal device relies on balancing gel formation of the matrices (hydration rate), maintaining pressure from the biasing system, control over the area of the matrices in contact with the ruminal fluids and the rate of erosion of dissolution.

Although the present invention and its advantages have been described in detail, it should be understood that various changes, substitutions and alterations can be made herein without departing from the spirit and scope of the invention as defined in the appended claims.

The present invention will be further illustrated in the following examples which are given for illustration purposes only and are not intended to limit the invention in any way.

EXAMPLES

Example 1

Four trials with biotin-containing capsules were tested on n=7 fistulated cattle.

Four intra-ruminal devices (capsules 1 to 4 corresponding to trials 1 to 4 respectively) were prepared. The ingredients in each of the capsules is shown in Table 1 below. The values in the table represent the amount of each ingredient as a percentage of each matrix.

TABLE 1

| Ingredients in intra-ruminal devices (capsules) 1 to 4 | | | | |
|---|---|---|---|---|
| Capsule number | 1 | 2 | 3 | 4 |
| Biotin | 8.131% | 8.335% | 8.335% | 8.500% |
| Sucrose Ester | 40.950% | 40.500% | 40.500% | 40.500% |
| Hydrated Aluminium Silicate | 31.850% | 31.500% | 31.500% | 31.500% |
| Lactose | 18.200% | 18.000% | 18.000% | 18.000% |
| Povidone | — | — | 0.865% | — |
| Colloidal Silicon Dioxide | 0.369% | 0.665% | — | 0.500% |
| Magnesium Stearate | 0.500% | 1.000% | 0.800% | 1.000% |

Kinetic performance of the capsule treatments was evaluated in 11 to 14 year old rumen-fistulated ex-dairy cows predominantly Friesian-Holstein with lesser amounts of Jersey. Weights of the fistulates range from 450 to 750 kg. They were grazed as a single mob on ryegrass clover pasture but which also contained plantain and buttercup. Feed intake was targeted at maintenance and water available as required.

Capsule pay-out using residual core length was measured using digital callipers on a weekly basis. Pay-out was determined by measuring from the front face of the orifice to the top of the plunger. Each capsule was measured twice in this way by rotating the capsule through 180°. Once measured, the capsules were immediately returned to the rumen. Measurement data was transcribed from the field recording sheets onto an electronic spreadsheet for loading into "Capper", a custom-made data analysis application for Microsoft Access. The transcribed data was verified by a second person to exclude transcription errors.

Capper calculated the average of the readings taken from each side of the barrel. This average plunger position in mm includes the thickness of the plunger and orifice plate. Release rate, coefficient of variation (CoV), linearity (minimum $r^2$) and capsule duration were analysed for the trial periods.

Trial details are summarised in Table 2.

TABLE 2

| Biotin capsule trial details. | | | | |
|---|---|---|---|---|
| Trial number | Trial 1 | Trial 2 | Trial 3 | Trial 4 |
| Period (days) | 7 to 259 | 7 to 196 | 7 to 196 | 7 to 119 |
| Orifice size (mm) | 8.00 | 9.00 | 9.00 | 9.00 |
| Orifice thickness (mm) | 1.50 | 1.50 | 1.50 | 1.50 |
| Plunger height (mm) | 10.00 | 10.00 | 10.00 | 10.00 |
| Rel. rate | 0.348-0.471 | 0.348-0.471 | 0.348-0.471 | 0.326-0.441 |
| Linearity | >=0.950 | >=0.950 | >=0.950 | >=0.950 |
| C of V | <=15.00 | <=15.00 | <=15.00 | <=15.00 |
| Mean rel. rate | 0.329 | 0.412 | 0.442 | 0.410 |
| Minimum linearity | 0.997 | 0.998 | 0.995 | 0.998 |
| C of V | 4.60 | 4.62 | 6.55 | 5.30 |

Note: Rel. rate refers to the target release rate in mm/day, that is, the plunger should move at this release rate in order to delivered the required amount of Biotin (20 mg per day #15%); Linearity is indicated by an R2 of each individual capsule of >0.95; C of V=Coefficient of variation (standard deviation divided by the mean of the sample set multiplied by 100) where the target C of V is <15%; Orifice thickness means thickness of the orifice plate at the end of the capsule.

All of the intra-ruminal devices trialed achieved controlled, sustained release of biotin as shown in FIGS. 1-4 corresponding to Trials 1-4 respectively.

Example 2

Three capsules (Z3209, Z3210 and Z3211) containing biotin as a model drug were prepared. The ingredients in each of the capsules is shown in Table 3 below. The values in the table represent the amount of each ingredient as a percentage of each matrix.

TABLE 3

Ingredients in each tablet used in the three intra-ruminal devices (capsules) prepared for this example

| Components | Concentration (% w/w) 170621-5 , 170630-1 (F020) |
|---|---|
| D-Biotin | 10.934 |
| Sucrose ester | 39.400 |
| Hydrated Aluminium Silicate (HAS) | 25.118 |
| Lactose Monohydrate 200 mesh | 22.064 |
| Povidone | 0.985 |
| Colloidal Silicon Dioxide | 0.500 |
| Magnesium Stearate | 1.000 |
| Total | 100 |

The processing parameters shown in Table 4 below were used to process the tablets.

TABLE 4

Processing parameters for the granulation of the tablets used in the capsules of this example

| Batch Number | Air Velocity (Pa) | Atomising Air Pressure (bar) | Spray Rate (g/min) | Amount of Water Sprayed (g) |
|---|---|---|---|---|
| 170621-5 | 5-30 | 2.0 | 39.9 | 558.60 |

The resulting tablets had an MPD of 257 and a Loss on Drying (LoD) value of 2.30% w/w.

The in vivo pay-out kinetics of the three capsules comprising the tablets prepared as described above was tested as per the method described in Example 1. The initial core length of the capsules was 93 mm.

Figure 5:
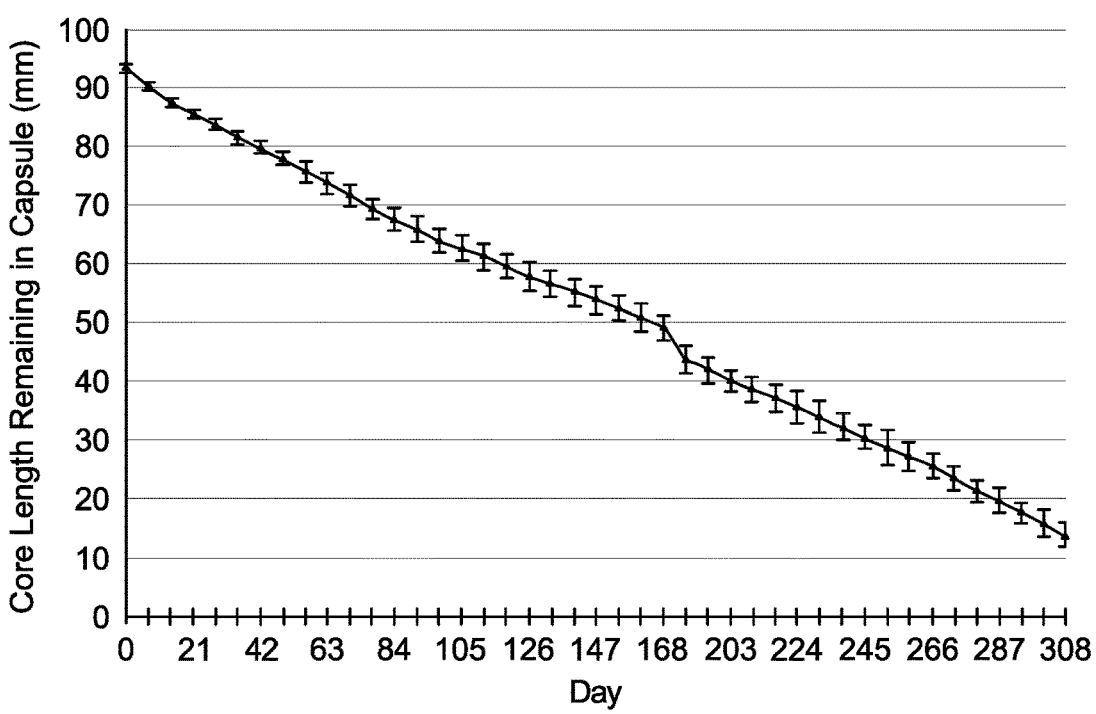
FIG. 5 shows the in vivo payout period in days of biotin from three intra-ruminal devices (capsules) Z3209, Z3210 and Z3211 in terms of the percentage of the core of the intra-ruminal device (capsule) that has been extruded (n=3, $R^2$ value is 0.9979).

The remaining core length (mm) of each capsule was measured every seven days and the data is shown in FIG. 5 which has a $R^2$ of 0.9982.

Figure 6:
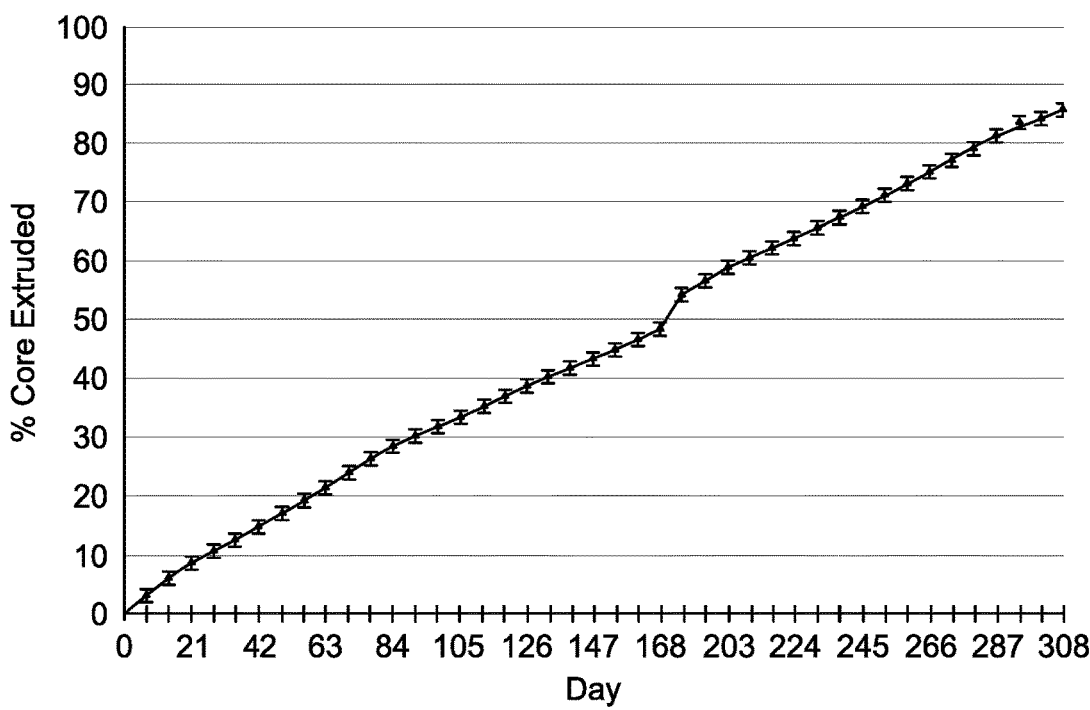
FIG. 6 shows the in vivo payout period in days of biotin from three intra-ruminal devices (capsules) Z3209, Z3210 and Z3211 in terms of the core length remaining in the intra-ruminal device (capsule) that has been extruded (n=3, $R^2$ value is 0.9982).

The data in FIG. 5 may also be presented in terms of the percentage of the core extruded over time as is shown FIG. 6, which has a $R^2$ of 0.9982 . . . . The percentage of the core extruded was calculated using the formula (Initial core length (Co)-Current core length (Cc))/Co.

Example 3—Evaluating the Effect of Manufacturing Conditions on the Properties of Tablets Containing Povidone K30 (Polyvinylpyrrolidone)

Seven lab-scale (1.5 kg) batches of D-Biotin tablets were manufactured using the equipment detailed in Table 6. D-Biotin was used a model active pharmaceutical ingredient (API) in this example.

TABLE 5

Main equipment used in the manufacture of the tablets in this example

| Stage | Description |
|---|---|
| Blending | Tanner Blender |
| Granulation | Glatt GPCG 1 Fluid-Bed Granulator |
| Compression | Single station press |

The compositions of the six formulations that were manufactured are detailed in Table 6 below.

A two level, two factor design of experiment (DOE) was performed in order to evaluate the influence of povidone and HAS concentrations. The DOE experiment design involved starting with a base formulation (F019) and increasing the amount of HAS to arrive at a new formulation (F016), or the amount of Povidone K30 to arrive at a new formulation (F018), or the amount of HAS and Povidone K30 to arrive at formulation (F017).

Figure 3:
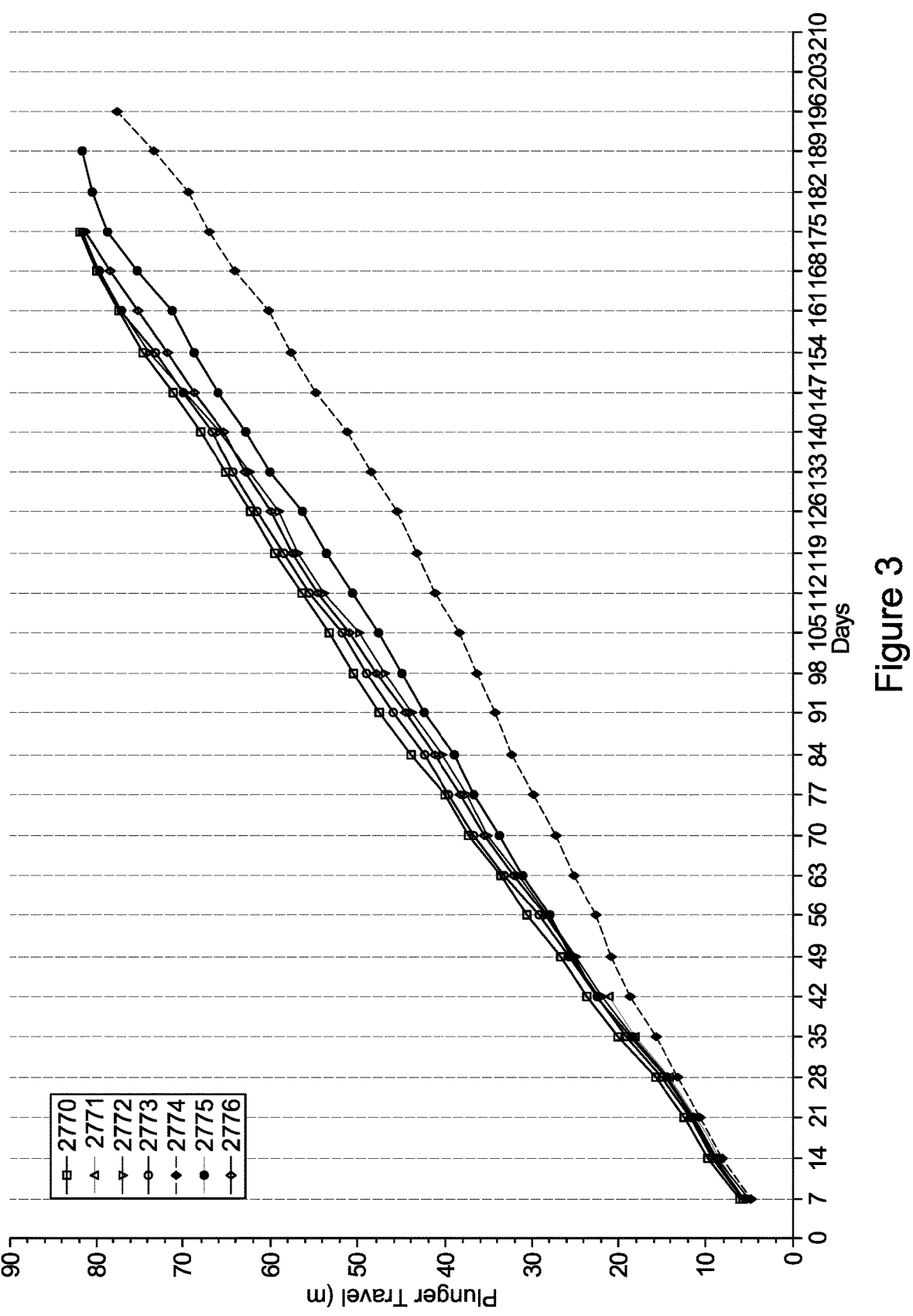
Figure 4:
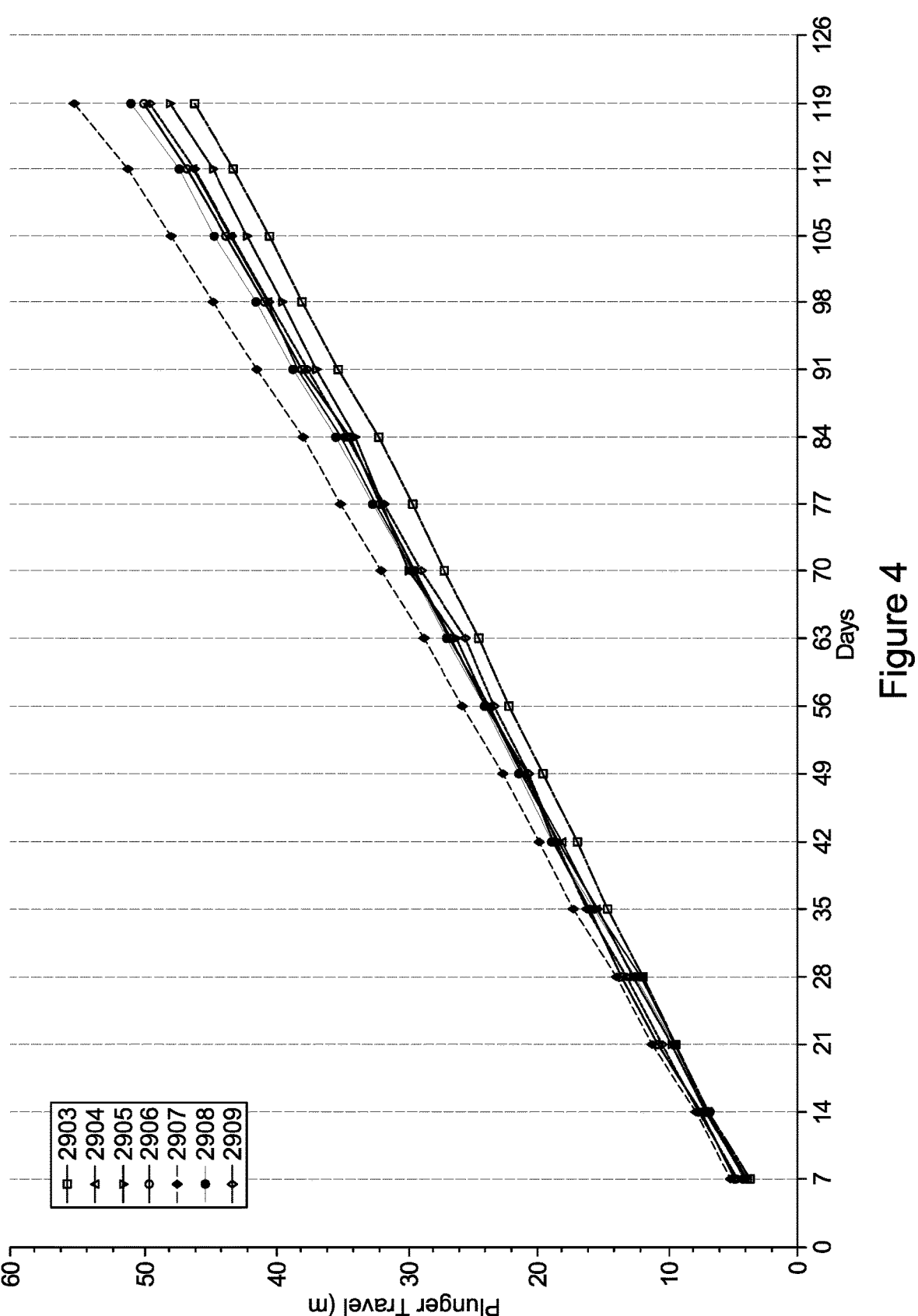

A process flow diagram illustrating the manufacturing process is provided in FIG. 3 for formulations F016-F020.

TABLE 6

Composition of D-Biotin Tablet Formulations

| Components | Concentration (% w/w) | | | | | |
|---|---|---|---|---|---|---|
| | 170615-1 (F015) | 170619-1 (F016) | 170621-2 (F017) | 170621-3 ( F018) | 170621-4 (F019) | 170621-5, 170630-1 (F020) |
| D-Biotin | 10.900* | 934 | 10.934 | 10.934 | 10.934 | 10.934 |
| Sucrose ester | 39.420 | 400 | 39.400 | 39.400 | 39.400 | 39.400 |
| Hydrated Aluminum Silicate (HAS) | 17.520 | 634 | 30.634 | 19.700 | 19.700 | 25.118 |
| Lactose Monohydrate 200 mesh | 30.660 | 533 | 15.563 | 26.497 | 28.467 | 22.064 |
| Povidone K30 | None | None | 1.970 | 1.970 | None | 0.985 |
| Colloidal Silicon Dioxide | 0.500 | 500 | 0.500 | 0.500 | 0.500 | 0.500 |
| Magnesium Sterate | 1.000 | 1.000 | 1.000 | 1.000 | 1.000 | 1.000 |
| Total | 100 | 100 | 100 | 100 | 100 | 100 |

Granulation

Processing parameters such as air velocity, atomising air pressure and spray rate were adjusted in order to provide granules of the required attributes. Air velocity was between 5 and 30 Pa. Atomising air pressure was 2.0 bar. Spray rate was between 39.6 and 44.9 g/min. The amount of water sprayed was between 555.07 and 628.51 g. The granules were dried at 36° C. and passed through a 14 mesh screen. The granules were analysed for particle size and LoD. The results are summarised in Table 7.

TABLE 7

| Characterisation of granules | | | |
| --- | --- | --- | --- |
| Formulation | Batch Number | MPD (μm) | LoD (% w/w ) |
| F015 | 170616-1 | 311 | 2.00 |
| F016 | 170619-1 | 340 | 2.51 |
| F017 | 170621-2 | 326 | 2.80 |
| F018 | 170621-3 | 327 | 2.41 |
| F019 | 170621-4 | 291 | 2.10 |
| F020 | 170621-5 | 257 | 2.30 |
| | 170630-1 | 231 | 2.20 |

Blending

For batch 170616-1, D-Biotin was added through a 40 mesh hand screen into the dried granules and mixed for 10 minutes in the tanner blender at 25 rpm speed.

A summary of the in process tablet weight and tablet thickness data obtained for each batch is detailed in Table 8. The individual tablet target weight for each batch was 3.925 g with an in process range of #3% (3.807-4.043 g). It can be seen that all of the batches were manufactured within these limits.

TABLE 8

| In process weight and thickness data for tablets of different formulations | | | |
| --- | --- | --- | --- |
| Formulation Number | Batch Number | Tablet Weight Range (g) | Tablet Thickness Range (mm) |
| F015 | 170616-1 | 3.8669-3.9589 | 6.42-6.60 |
| F016 | 170619-1 | 3.9321-3.9651 | 6.39-6.47 |
| F017 | 170621-2 | 3.9321-3.9651 | 6.39-6.47 |
| F018 | 170621-3 | 3.8972-3.9506 | 6.60-6.74 |
| F019 | 170621-4 | 3.9026-3.9380 | 6.53-6.67 |
| F020 | 170621-5 | 3.0912-3.9523 | 6.57-6.67 |
| | 170630-1 | 3.8794-3.9418 | 6.61-6.69 |

In-Vitro Capsule Testing

The formulations prepared above (F016-F020) were evaluated using a custom made 240 L stainless steel tank. The enclosed tank was thermostatically controlled to 39° C. and equipped with a piston. The piston drove a brush which wiped the outlet of the capsules in order to mimic the physical abrasion to the tablet stack, which is expected to occur in vivo.

Capsules were placed in stainless-steel housing units so that approximately 3 mm of the bristles from the brush passed into the outlet each time the brush passed beneath the capsules (every 10 minutes).

The piston speed was tailored so that the travel time across the tank was 12-15 seconds. The tank was equipped with a pump so that the media inside the tank was constantly recirculating throughout the study.

Capsules were run in media containing different concentrations of calcium.

Capsule pay-out was calculated by measuring the distance from the front of the outlet to the top of the plunger using digital callipers. Each capsule was measured twice in this way by rotating the capsule through 180° and the mean value was used to calculate pay-out rates.

Five capsules (intra-ruminal devices) for each formulation were assembled with a spring having a 1.3 kgf spring force and each capsule having a 9.0 mm outlet size.

The capsules were run in 4 mM calcium concentration and subsequently, the concentration of calcium in the tank was gradually increased every 3-4 days (to 9 mM, 16 mM and 27 mM) and the effect on capsule kinetics determined over 52 days.

Table 9 provides a summary of the in vitro tank results and the pay-out profiles of the capsules.

TABLE 9

| Summary of In Vitro Pay-out data | | | | | |
| --- | --- | --- | --- | --- | --- |
| Trial Number | Batch Number | Formulation | Mean Pay-out Rate (mm/day) [1] | Minimum $R^2$ | % CV[1] |
| X1927 | 170619-1 | F016 | 0.438 | 0.999 | 4.10 |
| X1928 | 170621-2 | F017 | 0.448 | 0.999 | 5.24 |
| X1929 | 170621-3 | F018 | 0.529 | 0.998 | 3.30 |
| X1930 | 170621-4 | F019 | 0.489 | 0.998 | 1.87 |
| X1931 | 170621-5 | F020 | 0.465 | 0.998 | 1.96 |

[1] mean pay out from day 3 to day 52. C of V stands for Coefficient of variation: st deviation/mean * 100.

The high linearity values ($R^2$) in Table 13 indicate that the addition of calcium to the release media did not have a marked effect on capsule pay-out in vitro. Formulations F019 and F020 displayed particularly low CV values (<2%).

Figure 8:
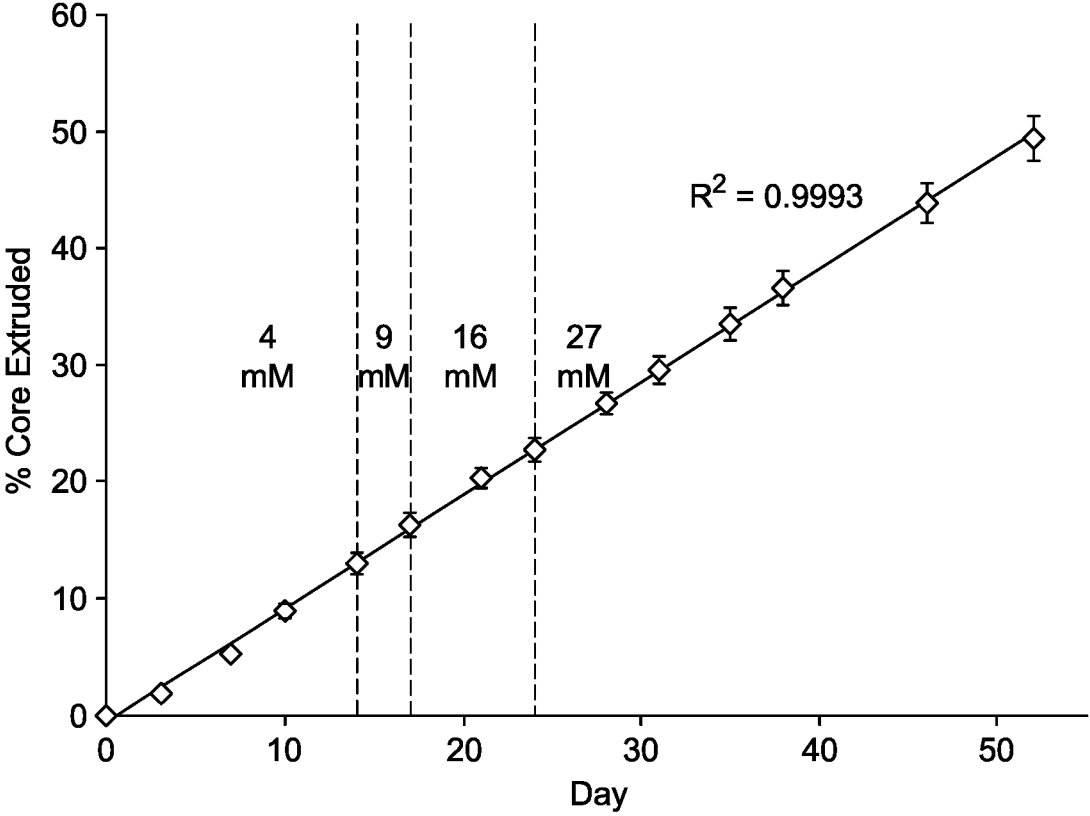
FIG. 8 the in vitro payout rate (expressed as a percentage of the core extruded on the y axis) as a function of time (in days on the x axis) of 5 replicate capsules (represented by different coloured lines and the codes Z3172, Z3173, Z3174, Z3175 and Z3176) comprising a non-ionic polymer, Polyox 301. The capsules were tested in a tank comprising water followed by 4 mM, 9 mM, 16 mM and 27 mM solutions of calcium ions respectively, where the change between the solutions is indicated by the dashed vertical lines in the graph. The payout of the capsules was substantially unaffected by the increased concentration of calcium in solution.

The mean payout from the five capsules corresponding to formulation F016 are shown in FIG. 8. FIG. 8 shows that formulation F016 resulted in a substantially linear payout with an R2 value of 0.9993 despite an increase in calcium ion in the tank over the test period.

Evaluation of In-Vivo Payout Performance

In vivo performance of five batches of tablets (corresponding to batch numbers 170619-1, 170621-2, 170621-3, 170621-4, and 170621-5 whose formulation is described herein) were assessed in fistulated cattle (N=3).

For each of the 5 batches, fourteen tablets were assembled in capsules with a spring having a 1.3 kgf spring strength and the capsule having a 7.0 mm outlet.

Table 10 summarises the data obtained to date (up to day 77).

The mean pay-out rates for all 5 batches were within the target pay-out range.

| | | | | | Mean | | | |
| --- | --- | --- | --- | --- | --- | --- | --- | --- |
| | | | Orifice | Target Pay- | Actual | Expected | Minimum | |
| Trial | Batch | Formu- | Size | out Rate | Pay-out | Expiry | $R^2$ (Day | % |
| Number | Number | lation | (mm) | (mm/day)[1] | (mm/day) | (Days) | 7 to 77) | $CV^{@}$ |
| X1932 | 170619-1 | F016 | 7.0 | 0.268-0.362 | 0.278 | 322 | 0.997 | 3.14 |
| X1933 | 170621-2 | F017 | 7.0 | 0.260-0.351 | 0.273 | 328 | 0.996 | 1.92 |
| X1934 | 170621-3 | F018 | 7.0 | 0.260-0.351 | 0.319 | 291 | 0.998 | 2.44 |
| X1935 | 170621-4 | F019* | 7.0 | 0.270-0.365 | 0.294 | 314 | 0.985 | 3.85 |
| X1936 | 170621-5 | F020 | 7.0 | 0.268-0.362 | 0.301 | 306 | 0.997 | 6.26 |

Summary of In Vivo Pay-out Data

[1]delivers a dose of 20 mg/day D-Biotin for 300 days.
[@]mean pay put from day 7 to 77.

CONCLUSION

Tablets from batch numbers 170621-2 (high HAS, high Povidone) and 170621-4 (low HAS, no Povidone) were tested for stability (40° C./75% relative humidity (RH)) for 2 months and after 2 months they were tested for the amount of D-Biotin remaining, reported as a % label claim of D-Biotin.

The results are summarised in Table 11. From the results, it can be concluded that having 2% w/w Povidone in the formulation (F017: 170621-2), did not affecting the stability of the tablets, when compared to the formulation (F019: 170621-4) without Povidone.

TABLE 11

Stability assay results for D-biotin tablets
(Time = 10 weeks storage at 40° C./75% RH)

| Batch Number | Tablet Assay Results (% w/w) | % Label Claim in the tablet (Calculated) | % Label Claim (Calculated based on API potency result)* |
| --- | --- | --- | --- |
| 170621-2 | 10.7084 | 97.9 | 99.2 |
| 170621-4 | 10.6120 | 97.1 | 98.4 |

*D-Biotin was tested for the potency and the result was 98.7% w/w. The formulations were manufactured by assuming potency of D-Biotin 100% w/w.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

The invention claimed is:

1. An intra-ruminal device comprising
a body substantially impervious to rumen fluid, the body comprising a barrel, at least one outlet, and at least one matrix in the barrel,
a compression arrangement within the body adapted to bias the at least one matrix in the barrel to the at least one outlet, and
at least one variable geometry device dependent from the body to assist rumen retention;
wherein the at least one matrix in the barrel comprises at least one active ingredient, 5% to 50% by weight of a gel former comprising a sucrose fatty acid ester, and 5% to 40% by weight of at least one clay mineral; and
wherein the device is configured to provide a sustained delivery of the one or more active ingredients over a period greater than 150 days.

2. The intra-ruminal device of claim 1, wherein the clay mineral is selected from the group consisting of kaolin, talc, nontronite, saponite, sepiolite, palygorskite, halloysite, vermiculite, muscovite, illite, hectorite, montmorillonite, bentonite, beidellite, volkonskoite, laponite, sauconite, magadiite, kanyaite, ledikite, nacrite, attapulgite, or zeolite, or a combination thereof.

3. The intra-ruminal device of claim 1, wherein the clay mineral is kaolin.

4. The intra-ruminal device of claim 1, wherein the device provides sustained delivery of the one or more active ingredients over at least 250 days.

5. The intra-ruminal device of claim 4, wherein the sustained delivery is linear with a linearity value of >0.95.

6. The intra-ruminal device of claim 1, wherein the device provides sustained delivery of the one or more active ingredients over at least 300 days.

7. The intra-ruminal device of claim 6, wherein the sustained delivery is linear with a linearity value of >0.95.

8. The intra-ruminal device of claim 1, wherein the compression arrangement within the body is adapted to bias the at least one matrix in the barrel to the at least one outlet at a rate of 0.1 mm to 1.2 mm per day.

9. The intra-ruminal device of claim 1, wherein the compression arrangement within the body is adapted to bias the at least one matrix in the barrel to the at least one outlet at a rate of 0.1 mm to 0.8 mm per day.

10. The intra-ruminal device of claim 1, wherein the compression arrangement within the body is adapted to bias the at least one matrix in the barrel to the at least one outlet at a rate of 0.2 mm to 0.6 mm per day.

11. The intra-ruminal device of claim 1, wherein the at least one active ingredient is selected from the group consisting of parasiticides, non-steroidal anti-inflammatories, antibiotics, probiotics, antivirals, anthelmintics, steroid hormones, metabolic regulators, enzyme inhibitor, rumen methane inhibitors/regulators, ruminal fermentation modifiers, productivity regulators, vitamins and minerals, or a combination thereof.

12. The intra-ruminal device according to claim 1, wherein the at least one active ingredient is a parasiticide.

13. The intra-ruminal device of claim 12, wherein the parasiticide is an anthelmintic selected from the group consisting of benzimidazoles, imidazothiazoles, tetrahydropyrimidines, macrocyclic lactones, salicylanides, substituted phenols, aromatic amides, isoquinolines, amino acetonitriles and spiroindoles, or a combination thereof.

14. A method of assembling a controlled delivery intraruminal device according to claim 1, the method comprising a) granulating a mixture comprising at least one active ingredient, 5% to 50% by weight of a gel former comprising a sucrose fatty acid ester, and 5% to 40% by weight of at least one clay mineral, b) drying the granules, c) passing the granules through a sieve, and d) tabletting the granules into at least one matrix, and e) loading the at least one matrix into the body of an intra-ruminal device.

15. The method of claim 14, wherein the mixture further comprises one or more excipients.

16. The intra-ruminal device of claim 1, wherein the sustained delivery is linear with a linearity value of >0.95.

17. The intra-ruminal device of claim 1, wherein the compression arrangement within the body is adapted to bias the at least one matrix in the barrel to the at least one outlet at a rate of 0.1 mm to 1.2 mm per day.

18. The intra-ruminal device of claim 1, wherein the compression arrangement within the body is adapted to bias the at least one matrix in the barrel to the at least one outlet at a rate of 0.1 mm to 0.8 mm per day.

19. The intra-ruminal device of claim 1, wherein the compression arrangement within the body is adapted to bias the at least one matrix in the barrel to the at least one outlet at a rate of 0.2 mm to 0.6 mm per day.

20. The intra-ruminal device of claim 1, wherein the gel former is present at 20% to 50% by weight.

* * * * *